US010202604B2

(12) United States Patent
Tang et al.

(10) Patent No.: US 10,202,604 B2
(45) Date of Patent: Feb. 12, 2019

(54) METHODS OF USING MICRORNA-141

(71) Applicants: Dean Tang, Williamsville, NY (US); Can Liu, Austin, TX (US)

(72) Inventors: Dean Tang, Williamsville, NY (US); Can Liu, Austin, TX (US)

(73) Assignee: Stemirna Therapeutics Co., Ltd., Shanghai (CN)

( * ) Notice: Subject to any disclaimer, the term of this patent is extended or adjusted under 35 U.S.C. 154(b) by 0 days.

(21) Appl. No.: 15/606,638

(22) Filed: May 26, 2017

(65) Prior Publication Data

US 2017/0342417 A1    Nov. 30, 2017

Related U.S. Application Data

(60) Provisional application No. 62/341,634, filed on May 26, 2016.

(51) Int. Cl.
C12N 15/11       (2006.01)
A61K 48/00       (2006.01)
C07H 21/02       (2006.01)
C07H 21/04       (2006.01)
C12N 15/113      (2010.01)

(52) U.S. Cl.
CPC ........ *C12N 15/1135* (2013.01); *C12N 15/113* (2013.01); *C12N 2310/141* (2013.01)

(58) Field of Classification Search
CPC .............. C12N 15/1135; C12N 15/113; C12N 2310/141
USPC ........................................... 514/44; 536/23.1
See application file for complete search history.

(56) References Cited

U.S. PATENT DOCUMENTS

2014/0018411 A1*   1/2014   Croce ................... C12N 15/111
                                                                    514/44 A

OTHER PUBLICATIONS

Liu et al. (Nature Communications, 8:14270, doi:10.1038/ncomms14270 (2017).*
Liu et al. (PLOS, 2014 vol. 9:1-10).*
Lin et al. (BMC Cancer, 2014 vol. 14:879, pp. 1-10).*
Mei et al. (FEBS Letters, 2014 vol. 588:3055-3061).*
Kreso and Dick. Evolution of the cancer stem cell model. Cell Stem Cell 2014; 14 (3):275-91.
Tang DG. Understanding cancer stem cell heterogeneity and plasticity. Cell Res 2012; 22 (3):457-72.
Saini et al. miRNA-708 control of CD44(+) prostate cancer-initiating cells. Cancer Res 2012;72 (14):3618-30.
Li et al. PC3 human prostate carcinoma cell holoclones contain self-renewing tumor-initiating cells. Cancer Res 2008; 68 (6):1820-5.
Liu and Tang. MicroRNA regulation of cancer stem cells. Cancer Res 2011; 71(18):5950-4.
Patrawala et al. Highly purified CD44+0 prostate cancer cells from xenograft human tumors are enriched in tumorigenic and metastatic progenitor cells. Oncogene 2006; 25 (12):1696-708.

(Continued)

Primary Examiner — Terra C Gibbs

(57) ABSTRACT

Provided herein are methods of treating a cancer in an individual. A microRNA-141 oligonucleotide or mimic that increases the expression of microRNA-141 in the cancer cell is administered to the individual. Also provided is a method of inhibiting proliferation of a cancer cell and treating a cell associated with a cancer. The cell is contacted with the microRNA-141 oligonucleotide or mimic.

16 Claims, 38 Drawing Sheets

Specification includes a Sequence Listing.

(56) References Cited

OTHER PUBLICATIONS

Patrawala et al. Hierarchical organization of prostate cancer cells in xenograft tumors: the CD44+alpha2beta1+ cell population is enriched in tumor-initiating cells. Cancer Res 2007; 67 (14):6796-805.
Qin et al. The PSA(-/lo) prostate cancer cell population harbors self-renewing long-term tumor-propagating cells that resist castration. Cell Stem Cell 2012;10 (5):556-69.
Liu et al. The microRNA miR-34a inhibits prostate cancer stem cells and metastasis by directly repressing CD44. Nat Med 2011;17 (2):211-5.
Liu et al. Systematic dissection of phenotypic, functional, and tumorigenic heterogeneity of human prostate cancer cells. Oncotarget 2015; 6 (27): 23959-86.
Hayes et al. MicroRNAs in cancer: biomarkers, functions and therapy. Trends Mol Med 2014; 20(8):460-9.
Liu C et al. Distinct microRNA expression profiles in prostate cancer stem/progenitor cells and tumor-suppressive functions of let-7. Cancer Res 2012; 72(13): 3393-404.
Adams et al. Aberrant regulation and function of microRNAs in cancer. Curr Biol 24, R762-776 (2014).
Aigner et al. The transcription factor ZEB1 (deltaEF1) promotes tumour cell dedifferentiation by repressing master regulators of epithelial polarity. Oncogene 26, 6979-88 (2007).
Ambs et al. Genomic profiling of microRNA and messenger RNA reveals deregulated microRNA expression in prostate cancer. Cancer Res 68, 6162-6170 (2008).
Bracken et al. EZH2 is downstream of the pRB-E2F pathway, essential for proliferation and amplified in cancer. EMBO J 22, 5323-5335 (2003).
Bracken et al. Genome-wide identification of miR-200 targets reveals a regulatory network controlling cell invasion. EMBO J 33, 2040-2056 (2014).
Burk et al. A reciprocal repression between ZEB1 and members of the miR-200 family promotes EMT and invasion in cancer cells. EMBO Report 9, 582-589 (2008).
Cao et al. Coordinated regulation of polycomb group complexes through microRNAs in cancer. Cancer Cell 20, 187-199 (2011).
Cao et al. Repression of E-cadherin by the polycomb group protein EZH2 in cancer. Oncogene 27, 7274-7284 (2008).
Charafe-Jauffret et al. Gene expression profiling of breast cell lines identifies potential new basal markers. Oncogene 25, 2273-84 (2006).
Cheng et al. Circulating plasma MiR-141 is a novel biomarker for metastatic colon cancer and predicts poor prognosis. PLoS one 6, e17745 (2011).
Collins et al. Prospective identification of tumorigenic prostate cancer stem cells. Cancer Res 65, 10946-10951 (2005).
Deng, Q. & Tang, D.G. Androgen receptor and prostate cancer stem cells: biological mechanisms and clinical implications. Endocr Relat Cancer 22, T209-220 (2015).
Domingo-Domenech et al. Suppression of acquired docetaxel resistance in prostate cancer through depletion of notch- and hedgehog-dependent tumor-initiating cells. Cancer Cell 22, 373-388 (2012).
Fang, Y.X., & Gao, W.Q. Roles of microRNAs during prostatic tumorigenesis and tumor progression. Oncogene 33, 135-147 (2014).
Friedl, P. & Alexander, S. Cancer invasion and the microenvironment: plasticity and reciprocity. Cell 147, 992-1009 (2011).
Gregory et al. The miR-200 family and miR-205 regulate epithelial to mesenchymal transition by targeting ZEB1 and SIP1. Nat Cell Biol 10, 593-601 (2008).
Hao et al. Improvement of prostate cancer detection by integrating the PSA test with miRNA expression profiling. Cancer Invest 29, 318-324 (2011).
Iorio et al. MicroRNA signatures in human ovarian cancer. Cancer Res 67, 8699-8707 (2007).
Jolly et al. Coupling the modules of EMT and stemness: A tunable 'stemness window' model. Oncotarget 6, 25161-25174 (2015).
Kalluri, R. & Weinberg, R.A. The basics of epithelial-mesenchymal transition. J Clin Invest 119, 1420-1428 (2009).

Kasinski et al. A combinatorial microRNA therapeutics approach to suppressing non-small cell lung cancer. Oncogene 34, 3547-3555 (2015).
Kleer et al. EZH2 is a marker of aggressive breast cancer and promotes neoplastic transformation of breast epithelial cells. Proc. Natl. Acad. Sci. USA 100, 11606-11611 (2003).
Korpal et al. Direct targeting of Sec23a by miR-200s influences cancer cell secretome and promotes metastatic colonization. Nat Med 17, 1101-1108 (2011).
Zhang et al. Stem cell and neurogenic gene-expression profiles link prostate basal cells to aggressive prostate cancer Nat Commun, 7:10798. (2016).
Lim et al. RTerseaanrchs acrtricileptome analyses of mouse and human mammary cell subpopulations reveal multiple conserved genes and pathways Breast Cancer Res 12, R21 (2010).
Pencheva, N. & Tavazoie, S.F. Control of metastatic progression by microRNA regulatory networks. Nat Cell Biol 15, 546-554 (2013).
Liu et al. MicroRNA93 regulates proliferation and differentiation of normal and malignant breast stem cells. PLoS Genet. 8, e1002751 (2012).
Liu et al. reast cancer stem cells transition between epithelial and mesenchymal states reflective of their normal counterparts. Stem Cell Reports 2, 78-91 (2013).
Lovisa et al. Epithelial-to-mesenchymal transition induces cell cycle arrest and parenchymal damage in renal fibrosis. Nat Med. 21, 998-1009 (2015).
Ma et al. Tumour invasion and metastasis initiated by microRNA-10b in breast cancer. Nature 449, 682-688 (2007).
Madhavan et al. Circulating miRNAs as surrogate markers for circulating tumor cells and prognostic markers in metastatic breast cancer. Clin Cancer Res 18, 5972-5982 (2012).
Medema, J.P. Cancer stem cells: the challenges ahead. Nat Cell Biol 15, 338-344(2013).
Mitchell et al. Circulating microRNAs as stable blood-based markers for cancer detection. Proc Natl Acad Sci USA 105, 10513-10518 (2008).
Onder et al. Loss of E-cadherin promotes metastasis via multiple downstream transcriptional pathways. Cancer Res 68, 3645-54 (2008).
Ozen et al. Widespread deregulation of microRNA expression in human prostate cancer. Oncogene 27, 1788-1793 (2008).
Park et al. The miR-200 family determines the epithelial phenotype of cancer cells by targeting the E-cadherin repressors ZEB1 and ZEB2. Genes & Dev 22, 894-907 (2008).
Patrawala et al. Side population is enriched in tumorigenic, stem-like cancer cells, whereas ABCG2+ and ABCG2-cancer cells are similarly tumorigenic. Cancer Res 65, 6207-6219 (2005).
Zhang et al. TGF-β-induced epithelial-to-mesenchymal transition proceeds through stepwise activation of multiple feedback loops. Sci. signaling 7, ra91 (2014).
Porkka et al. MicroRNA expression profiling in prostate cancer. Cancer Res. 67, 6130-6135 (2007).
Rajasekhar et al. Tumour-initiating stem-like cells in human prostate cancer exhibit increased NF-κB signalling. Nat Commun 2, 162 (2011).
Rottner et al. Actin dynamics and turnover in cell motility. Curr Opin Cell Biol 23, 569-578 (2011).
Rybak et al. Prostate cancer stem cells: deciphering the origins and pathways involved in prostate tumorigenesis and aggression. Oncotarget 6, 1900-1919 (2015).
Yun et al. Signalling pathway for RKIP and Let-7 regulates and predicts metastatic breast cancer. EMBO J 30, 4500-4514 (2011).
Sanz-Moreno et al. The plasticity of cytoskeletal dynamics underlying neoplastic cell migration Curr Opin Cell Biol 22, 690-696 (2010).
Selth et al. Discovery of circulating microRNAs associated with human prostate cancer using a mouse model of disease. Int J Cancer 131, 652-661 (2012).
Szczyrba et al. The microRNA profile of prostate carcinoma obtained by deep sequencing. Mol. Cancer Res. 8, 529-538 (2010).
Thiery, J.P. & Sleeman, J.P., Complex networks orchestrate epithelial-mesenchymal transitions Nat Rev Mol Cell Biol 7, 131-142 (2006).

(56) References Cited

OTHER PUBLICATIONS

Tong et al. MicroRNA profile analysis of human prostate cancers. Cancer Gene Ther 16, 206-216 (2009).
Vallejo et al. Targeting Notch signalling by the conserved miR-8/200 microRNA family in development and cancer cells. EMBO J 30, 756-769 (2011).
Varambally et al. The polycomb group protein EZH2 is involved in progression of prostate cancer. Nature 419, 624-629 (2002).
Waltering et al. Androgen regulation of micro-RNAs in prostate cancer. The Prostate 71, 604-614 (2011).
Wong et al. Module map of stem cell genes guides creation of epithelial cancer stem cells. Cell Stem Cell 2, 333-44 (2008).
Xiao et al. miR-141 modulates androgen receptor transcriptional activity in human prostate cancer cells through targeting the small heterodimer partner protein. The Prostate 72, 1514-1522 (2012).
Yu et al. Circulating breast tumor cells exhibit dynamic changes in epithelial and mesenchymal composition. Science 339, 580-584 (2013).

* cited by examiner

METHODS OF USING MICRORNA-141

CROSS-REFERENCE TO RELATED APPLICATIONS

This non-provisional application claims benefit of priority under 35 U.S.C. § 119(e) of provisional application U.S. Ser. No. 62/341,634, filed May 26, 2016, the entirety of which is hereby incorporated by reference.

BACKGROUND OF THE INVENTION

Field of the Invention

The present invention relates to the fields of molecular biology and oncology. More specifically, the present invention relates to methods of using microRNA-141 to suppress tumor growth and metastasis.

Description of the Related Art

Human cancers are heterogeneous containing cancer stem cells (CSCs) that possess high capacities for tumor propagation as well as metastasis (1-3). Metastasis causes >90% of cancer related deaths but the understanding of the molecular mechanisms that regulate metastasis remains limited. The invasion-metastasis cascade is a multistep cellular process that involves dissemination of cancer cells through the surrounding extracellular matrix, survival in the circulation, and initial seeding followed by subsequent expansion (colonization) in the foreign microenvironment. Recent evidence suggests that microRNAs (miRNAs), small (~20-22 nt) noncoding RNAs that modulate multiple biological processes, play important roles in regulating cancer stem cells, tumor development, and metastasis (4-7). Specific microRNAs, highlighted by miR-200 family, miR-34a, let-7, miR-10b, and miR-93 (8-17), may function as either promoters or suppressors of metastasis via a variety of mechanisms.

In human prostate cancer (HPCa), several cancer stem cell populations have been reported using cell surface markers (e.g., CD44, CD133, integrin $\alpha_2\beta_1$, ABCG2, etc), functional assays including side population (SP) and Aldefluor, and reporter-based lineage tracing strategies (18-26). These prostate cancer stem cell (PCSC) populations have been shown to possess high clonal, clonogenic, tumor propagating, invasive, and metastatic activities and to be refractory to castration, docetaxel, and many other therapeutics. Nevertheless, how prostate cancer stem cells are molecularly regulated, e.g., by microRNAs, remains poorly understood.

In a previous microRNA library screening for prostate cancer stem cell-regulating microRNAs, miR-34a and let-7, both being potent tumor suppressors, are prominently under-expressed in several prostate cancer stem cell populations and negatively regulate prostate cancer stem cell activity, tumor growth and metastasis (13,14).

The miR-200 family, which encompasses miR-200 a, b, and c, miR-429, and miR-141, is among the first to be reported as important negative regulators of epithelial to mesenchymal transition (EMT) (8-10), an essential developmental process also implicated in cancer metastasis (27, 28). Although the prevailing view is that under-expression of miR-200s promotes epithelial to mesenchymal transition and metastasis, there are also reports of upregulated expression and potential metastasis-promoting effects of miR-200 members in different types or subtypes of cancer (11,29). In addition, serum levels of miR-141 and other miR-200 family members have been positively associated with the different clinical outcomes of prostate, ovarian, colon and breast cancers (30-32).

The prior art is deficient in methods of using miR-141 as a tumor suppressor. The present invention fulfills this long-standing need and desire in the art.

SUMMARY OF THE INVENTION

The present invention is directed to a method of treating cancer in an individual. The method comprises administering to the individual a pharmacologically effective amount of a microRNA-141 oligonucleotide or a micro-RNA-141 or a pharmaceutical composition thereof that increases the expression of microRNA-141 in a cell associated with the cancer.

The present invention is directed further to a method of inhibiting proliferation of a cancer cell in an individual. The method comprises administering to the individual a pharmacologically effective amount of a microRNA-141 oligonucleotide or a micro-RNA-141 mimic or a pharmaceutical composition thereof that increases the expression of micro-RNA-141 in the cancer cell.

The present invention is directed further still to a method of inhibiting proliferation of a cell associated with cancer. The method comprising contacting the cell with a pharmacologically effective amount of a microRNA-141 oligonucleotide or a micro-RNA-141 mimic that increases the expression of microRNA-141 in the cancer cell of the individual.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1A shows the relative expression levels of miR-141 in cancer stem cell populations (compared to the corresponding marker-negative cells) in xenografts including CD44$^+$ populations from LAPC4, LAPC9, VCaP and Du145, $\alpha2\beta1+$ from Du145, and CD133$^+$ from LAPC4. FIG. 1B shows the relative expression levels of miR-141 in 4 AR+ and 4 AR− human prostate cancer cell types. Average % of CD44$^+$ cells (as determined by flow analysis; n=3-5) is indicated for each cell type (UD, undetectable). FIG. 1C shows the relative expression levels of miR-141 in CD44$^+$ cells (as % of the corresponding CD44-cells) from 21 primary Human prostate cancer samples. FIGS. 1D-1F shows that miR-141 inhibits clonal and clonogenic properties of CD44$^+$ Du145 cells. Purified CD44$^+$ Du145 cells were transfected with NC or miR-141 oligos (30 nM, 48 h) and then plated for clonal (1D & 1E) and sphere (1F) assays. Bars represent mean±SD. *, P<0.05; , P<0.01. FIGS. 1G-1J shows that miR-141 inhibits prostate tumor regeneration and growth. Shown are tumor images, cell numbers injected (100,000 cells per injection for all models), site of injection (s.c, subcutaneously) and days (d) when tumors were harvested. Tumor weight and incidences with corresponding P values are also indicated. ns, not significant. FIGS. 1K-1M show that miR-141 inhibits clonal and clonogenic properties of primary CD44$^+$ HPCa cells. Purified CD44$^+$ HPCa202 cells were infected with Lenti-ctl or Lenti-141 (MOI 10, 72 h) and plated for clonal assay (1K) or sphere assays in Matrigel (1L & 1M). For 1st generation (1°) sphere assays, 1,000 cells per well were plated in triplicate for each group in 12-well plate and results scored in 11 days. For 2nd generation (2°), the 1° spheres were harvested, digested with Collagenase and Trypsin into single cells, 1,000 cells/well were plated, and results scored in 10 days. Quantification of the colonies was plotted (1 L; P<0.01).

FIGS. 2A-2D show that miR-141 inhibits lung metastasis of CD44$^{hi}$ PC3 cells. FACS-purified CD44$^{hi}$ luciferase/GFP double-tagged PC3 cells were infected with Lenti-141 or Lenti-ctl (MOI 10) and 100,000 cells each were injected into the DP of NOD/SCID mice (n=9). Tumor growth and metastasis were monitored using bioluminescence imaging (IVIS). FIGS. 2A-2B show the representative images and quantification (in total photon flux) of primary tumors before termination of the experiment. FIGS. 2C-2D show the representative images (FIG. 2C) and quantification (FIG. 2D) of lung metastasis with the primary tumors covered. In a, 4 animals showed lung metastasis without their primary tumors covered. Insets in (FIG. 2D) are the representative GFP IHC images in the lungs (note significantly reduced GFP+ metastatic foci in the Lenti-141 lung). FIG. 2E shows that miR-141 inhibits lung metastasis of CD44$^+$ Du145 cells. CD44$^+$ Du145 cells were infected with Lenti-ctl or Lenti-141 (MOI 10; 72 h) and cells were then injected into the DP of male NOD/SCID mice. Mice were terminated at day 56 and organs including lung were harvested for analyzing metastasis. Shown were representative IHC images of humanspecific Ki-67 staining. FIGS. 2F-2I show that miR-141 inhibits LAPC9 metastasis. LAPC9-GFP cells were infected with TRIPZ-NS or TRIPZ-141 inducible lentivirus (MOI 10, 72 h) and CD44$^+$ cells were purified out by FACS. 100,000 cells each were injected into the DP of NOD/SCID mice and, from day 16 on, two groups of mice were treated with Dox (200 mg/kg body weight in feed). Tumor volumes were measure twice weekly (FIG. 2F). Mice were terminated at day 40 and endpoint tumors were harvested and weighted (FIG. 2G; incidence indicated in bars). Lungs (and LN and some other organs) were harvested (FIG. 2H) to analyze metastasis by assessing GFP+ metastasis foci (FIG. 2I).

FIGS. 3A-3B show qPCR analysis of epithelial to mesenchymal transition markers in bulk (FIG. 3A) or CD44$^+$ (FIG. 3B) Du145 cells transfected with the miR-141 oligos (30 nM; 48 h). Results were presented as the relative expression levels over the cells transfected with the NC oligos. FIG. 3C shows western blotting of E-Cadherin and ZEB-1 in PC3 and Du145 cells transfected with NC (60 nM) or miR-141 (30 or 60 nM) oligos (48 h). GAPDH was used as control and the relative protein levels after normalizing to GAPDH and NC controls were indicated below each lane. FIG. 3D shows a schematic of predicted miR-141 and miR-34a binding sites in the CD44 3'-UTR. Shown below is the actual sequence in the region with the mutated miR-141 binding sequence indicated in grey (below). FIG. 3E shows luciferase reporter assays in Du145 cells cotransfected with either wild-type CD44 3'-UTR or mutated 3'-UTR construct with miR-141 or NC oligos. FIG. 3F shows qPCR analysis of CD44 mRNA levels in the indicated PCa cells overexpressing miR-141 and in endpoint tumors generated from miR-141 overexpressing PCa cells. FIG. 3G shows representative Western blotting images of CD44 in PC3 and Du145 cells transfected with NC (60 nM) or miR-141 (30 and 60 nM) oligos harvested at two time points. FIG. 3H shows IF staining of CD44 (red) in PC3 cells transduced with Lenti-141 reveals a mutually exclusive expression pattern of CD44 and miR-141 (×200). Shown are representative images. FIG. 3I shows representative CD44 IHC images in two pairs of endpoint Du145 tumors derived from cells initially transduced with Lenti-141 or Lenti-ctl. FIG. 3J shows overexpression of a non-targetable CD44 cDNA partially 'rescues' the invasion-inhibitory effects of miR-141. Du145 cells were co-transfected with NC or miR-141 oligos (30 nM) together with pBabe empty vector or pBabe-CD44 vector. After 48 h, cells were harvested for invasion assays. Bars, mean±SD. *, P<0.05; **, P<0.01.

FIG. 4A shows experimental scheme of RNA-Seq in Du145 cells and subsequent data analysis. FIGS. 4T-4Y shows several examples of novel direct miR-141 targets identified, including cellcycle related (CDK6, FIG. 4T), Rho GTPase related (ARPC5, CDC42EP3, CDC42, and RAC1; FIGS. 4U-4W, metabolism related (PDHA1; FIG. 4X), and CD44 (FIG. 4Y). The black arrows indicate putative binding site(s) with a mismatch while the red arrows the perfectly matched target sites with its sequence alignment. For each gene, the NM number and the length of the 3'-UTR are indicated.

FIG. 5A shows that miR-141 reduces the protein levels of RAC1, CDC42, ARPC5 and CDC42EP3. Du145 cells transfected with NC or miR-141 oligos at the two doses and time intervals indicated were used in Western blotting. Indicated below are relative expression levels (normalized to respective GAPDH and compared to NC) of each protein determined by densitometric scanning of the individual bands. FIG. 5B shows that luciferase reporter assays in Du145 cells co-transfected with wild-type RAC1, CDC42, ARPC5, or CDC42EP3 3'-UTRs and 30 nM miR-141 or NC oligos. Bars, mean±SD. *$P<0.05$; **$P<0.01$. FIG. 5C shows that over-expression of RAC1 or CDC42 'rescued' the inhibitory effects of miR-141 on invasion. Du145 cells were co-transfected with NC or miR-141 oligos (30 nM) in combination with pcDNA3.1 (control) vector or pcDNA-RAC1 or pcDNA-CDC42 expression vector. After 48 h, cells were harvested for invasion assays. FIG. 5D shows that miR-141 expression inhibits the GTPase activities of RAC1 and CDC42 but not of RhoA. Du145 cells were infected with Lenti-141 or control lentivirus (MOI 10, 48 h) and then harvested to measure the Rho GTPase activities. Bars, mean±SD. *$P<0.05$. FIGS. 5E-5G shows that anti-miR-141 promotes PCa cell invasion. Du145 cells were transfected with the antisense oligos to NC or miR-141 (anti-141; 30 nM) and then used in invasion assays (FIG. 5E). In FIG. 5F and FIG. 5G Du145 cells were transfected with 10 nM of scramble siRNA control (siCon) or siRNAs targeting RAC1 (FIG. 5F) or CDC42 (FIG. 5G), either alone or in combination of anti-141 (30 nM). 48 h later, cells were harvested for invasion assays. Bars, mean±SD. *$P<0.05$; **$P<0.01$.

FIG. 6A: Putative binding site of miR-141 in EZH2 3'-UTR. FIG. 6B shows luciferase reporter assays in Du145 cells co-transfected with either wild-type EZH2 3'-UTR or the 3'-UTR with the predicted miR-141 binding site mutated with miR-141 or control oligos. FIG. 6C is a qPCR analysis of EZH2 mRNA levels in CD44$^+$ PCa cells. Bars, mean±SD. *$P<0.05$; $P<0.01$. FIG. 6D shows over-expression of miR-141 in Du145 cells using either oligo transfection or lentiviral infection reduced EZH2 mRNA levels. Bars, mean±SD. $P<0.01$. FIG. 6E shows that miR-141 reduces EZH2 and SUZ12 protein levels. Western blotting was performed in PC3 and Du145 cells transfected with NC (60 nM) or miR-141 (30 or 60 nM) oligos (72 h). Relative protein levels were measured by densitometry and normalized to GAPDH levels (indicated below). FIG. 6F is a GSEA showing the enrichment of miR-141 downregulated genes in the SUZ12 Targets gene set. FIG. 6G shows that the EZH2 inhibitor DZNep inhibits PCa cell invasion. Du145 cells plated one day before were treated with 1, 2, and 5 μM of DZNep for 96 h and then cells were harvested for invasion assays. $P<0.01$. Inset, WB showing reduced EZH2 proteins by DZNep. FIG. 6H shows that EZH2 knockdown inhibits PCa cell invasion that can be partially overcome by anti-141. Du145 cells were transfected with 10 nM scramble siRNA (siCon) or EZH2-targeting siRNAs (siEZH2) or siEZH2 plus anti-miR-141 (30 nM). 48 h later, cells were harvested for invasion assays. Bars, mean±SD. $P<0.01$. FIG. 6I shows that EZH2 overexpression partially 'rescues' the inhibitory effects of miR-141 on invasion. Du145 cells were co-transfected with 30 nM NC or miR-141 oligos together with empty vector or pCMV-EZH2 construct. After 48 h, cells were harvested for invasion assay. Bars, mean±SD. **$P<0.01$.

FIGS. 7A-7B show that miR141 mimics inhibit the proliferation and invasion of 95-D lung cancer cells, respectively. FIGS. 7C-7D show that miR141 mimics inhibit the proliferation and invasion of NCI-H358 lung cancer cells, respectively. FIGS. 7E-7F show that miR141 mimics inhibit the proliferation and invasion of NCI-H446 non-small lung cancer cells, respectively, where 141-1/2 is the mimic of miR141. N is the non-sense mimic, M is medium control, B is the black control **means p value is <<0.01 comparing with nonsense control.

FIGS. 8A-8B show that miR141 mimics inhibit the proliferation and invasion of Hep3B2.1-7 liver cancer cells, respectively. FIGS. 8C-8D show that miR141 mimics inhibit the proliferation and invasion of HepG2 liver cancer cells, respectively. FIGS. 8E-8F show that miR141 mimics inhibit the proliferation and invasion of HL-7702 liver cancer cells, respectively, where 141-1/2 is the mimic of miR141. N is the non-sense mimic, M is medium control, B is the blank control, **means p value is <<0.01 comparing with nonsense control.

DETAILED DESCRIPTION OF THE INVENTION

Figure 1A:
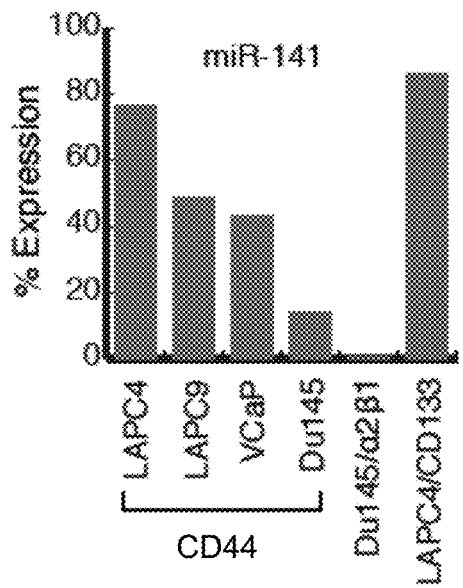
FIGS. 1A-1M shows under-expression of miR-141 in CD4$^+$ PCa cells and its PCa-suppressive functions.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, "treating" refer to administering to a individual a composition so that the individual has an improvement in the disease or condition. The improvement is any observable or measurable improvement. Thus, one of skill in the art realizes that a treatment may improve the individual's condition, but may not be a complete cure of the disease. Treating may also comprise treating individuals at risk of developing a disease and/or condition of the invention.

As used herein "composition" refers to a pharmaceutical composition comprising the microRNA-141 of the invention and optionally a pharmaceutically acceptable carrier. The compositions may be used for diagnostic or therapeutic applications. The administration of the pharmaceutical composition may be carried out by known methods, wherein a microRNA-141 is introduced into a desired target cell in vitro or in vivo.

As used herein "pharmacologically effective amount" refers to generally an amount effective to accomplish the intended purpose. However, the amount can be less than that amount when a plurality of the compositions are to be administered, i.e., the total effective amount can be administered in cumulative dosage units. The amount of active agent can also be more than the effective amount when the composition provides sustained release of the pharmacologically active agent. The total amount of a pharmacologically active agent to be used can be determined by methods known to those skilled in the art. However, because the compositions may deliver the pharmacologically active agent more efficiently than prior compositions, less amounts of active agent than those used in prior dosage unit forms or delivery systems can be administered to a subject while still achieving the same blood levels and/or therapeutic effects.

As used herein "contacting" refers to any suitable method of bringing a compound or a pharmaceutical composition into contact with a cell in vivo, in vitro or ex vivo. For in vivo applications, any known method of administration is suitable as known in the art.

In one embodiment, there is provided a method of treating cancer in an individual, comprising administering to the individual a pharmacologically effective amount of a micro-RNA-141 oligonucleotide or a micro-RNA-141 mimic or a pharmaceutical composition thereof that increases the expression of microRNA-141 in the cell associated with the cancer.

In this embodiment the cancer is a prostate cancer, a lung cancer or a liver cancer. Also in this embodiment the microRNA-141 oligonucleotide may have the sequence shown in SEQ ID NO: 1. In addition, administering the microRNA-141 oligonucleotide or the micro-RNA-141 mimic decreases the levels mRNA and protein level of CD44, EZH2, SUZ12, Rho GTPases or a combination thereof in the cancer cell. Furthermore, the cancer is prostate cancer and administering the microRNA-141 oligonucleotide or the micro-RNA-141 mimic upregulates E-Cadherin (CDH1), CLDN7, CLDN3, cytokeratin genes in a prostate cancer cell. Further still, the cancer is prostate cancer and administering the microRNA-141 oligonucleotide or the micro-RNA-141 mimic downregulates TGFB2, CDK6, SEC23A, ZEB1, MAP2K4, ARPC5, CDC42EP3, CDC42, RAC1, CD44 or VIM genes in a prostate cancer cell. Further still, administering the microRNA-141 oligonucleotide or the micro-RNA-141 mimic inhibits cell proliferation, inhibits invasion, inhibits migration, inhibits tumor growth, inhibits tumor regeneration, or inhibits metastatic potential or a combination thereof in the cancer.

In another embodiment, there is a method of inhibiting proliferation of a cancer cell in an individual, comprising administering to the individual a pharmacologically effective amount of a microRNA-141 oligonucleotide or a micro-RNA-141 mimic or a pharmaceutical composition thereof that increases the expression of microRNA-141 in the cancer cell.

In this embodiment the cancer cell is a prostate cancer, a lung cancer or a liver cancer. Also in this embodiment the microRNA-141 oligonucleotide may have the sequence shown in SEQ ID NO: 1. In addition, administering the microRNA-141 oligonucleotide or the micro-RNA-141 mimic inhibits invasion, migration, tumor growth, tumor regeneration, or metastatic potential of the cancer cell. Furthermore, administering the microRNA-141 oligonucleotide or the micro-RNA-141 mimic decreases the levels mRNA and protein level of CD44, EZH2, SUZ12, Rho GTPases or a combination thereof in the cancer cell. Further still, the cancer is prostate cancer and administering the microRNA-141 oligonucleotide or the micro-RNA-141 mimic upregulates E-Cadherin (CDH1), CLDN7, CLDN3, cytokeratin genes therein. Further still, the cancer is prostate cancer and administering the microRNA-141 oligonucleotide or the micro-RNA-141 mimic downregulates TGFB2, CDK6, SEC23A, ZEB1, MAP2K4, ARPC5, CDC42EP3, CDC42, RAC1, CD44 or VIM genes therein.

In yet another embodiment, there is provided a method of inhibiting proliferation of a cell associated with a cancer, comprising contacting the cell with a pharmacologically effective amount of a microRNA-141 oligonucleotide or a micro-RNA-141 mimic that increases the expression of microRNA-141 in the cell.

In this embodiment the cancer is a prostate cancer, a lung cancer or a liver cancer. Also in this embodiment the microRNA-141 oligonucleotide may have the sequence shown in SEQ ID NO: 1. In addition, contacting the cell with the microRNA-141 oligonucleotide or the micro-RNA-141 mimic decreases the levels mRNA and protein level of CD44, EZH2, SUZ12, Rho GTPases or a combination thereof in the cell. Furthermore, the cell is associated with a prostate cancer and contacting the microRNA-141 oligonucleotide or the micro-RNA-141 mimic upregulates E-Cadherin (CDH1), CLDN7, CLDN3, or cytokeratin genes therein. Further still, the cell is associated with a prostate cancer and contacting the microRNA-141 oligonucleotide or the micro-RNA-141 mimic downregulates TGFB2, CDK6, SEC23A, ZEB1, MAP2K4, ARPC5, CDC42EP3, CDC42, RAC1, CD44 or VIM genes therein. Further still, contacting the microRNA-141 oligonucleotide or the micro-RNA-141 mimic inhibits cell proliferation, inhibits invasion, inhibits migration, inhibits tumor growth, inhibits tumor regeneration, or inhibits metastatic potential or a combination thereof. The following examples are given for the purpose of illustrating various embodiments of the invention and are not meant to limit the present invention in any fashion.

Example 1

Material and Methods
Cells, Xenografts and Animals

Du145, LNCaP, PC3, PPC-1, VCaP cells were obtained from American Type Cell Culture and cultured in RPMI-1640 (Life Technologies, Carlsbad, Calif.) plus 7% fetal bovine serum (FBS) with the exception of VCaP, which were cultured in Dulbecco's Modified Eagles Medium (DMEM, Life Technologies) supplemented with 15% fetal bovine serum. Human xenograft prostate tumors, LAPC9

[bone metastasis; positive for androgen receptor (AR) and prostate-specific antigen (PSA)], LAPC4 (lymph node metastasis; AR+ and PSA+), and Du145 (bone metastasis; AR– and PSA–) were maintained in NOD/SCID mice. These cell and xenograft lines, which have been routinely utilized (13, 14, 18, 20, 21, 23, 25, 33) and authenticated by institutional CCSG Cell Line Characterization Core using short tandem repeat (STR) analysis and checked to be free of *mycoplasma* contamination using the Agilent (Santa Clara, Calif.) MycoSensor QPCR Assay Kit (cat.#302107). NOD/SCID mice were produced mostly from breeding colonies with occasional purchases from the Jackson Laboratories and maintained in standard conditions according to the Institutional Guidelines. All animal experiments were approved by Institutional Animal Care and Use Committee.

Human Primary Prostate Cancer (HPCa) Processing

All human prostate cancer samples used in this study were obtained from prostate cancer patients undergoing Da Vinci based radical prostatectomy with the written informed consent in accordance with federal and institutional guidelines and with the approved IRB protocol (MDACC LAB04-0498). The protocol for processing human prostate cancer samples to obtain high purity epithelial cancer cells was previously described (13).

RNA Isolation and Primers for qPCR Analysis

Total RNA was extracted using microRNA isolation kit (Life Technologies) according to the manufacturer's instructions. microRNA qPCRs were performed using TaqMan microRNA assays (Life Technologies). qPCR data for microRNAs were normalized to RNU48 whereas qPCR data for mRNAs were normalized to GAPDH.

Transient Transfection with Oligonucleotides

Prostate cancer cells were transfected with 30 nmol/L of miR-141 mirVana mimics or non-targeting negative control (NC) oligos, or the Anti-miR-141 and Anti-negative control antisense oligos (Life Technologies) using Lipofectamine RNAiMax (Life Technologies) per the manufacturer's instructions. After culturing for 48 h, transfected cells were harvested for in vitro and in vivo studies.

Lentiviral-Mediated Over-Expression of miR-141

Three different lentiviral vectors over-expressing miR-141 were generated, i.e., LentimiR-141 (based on Lenti-miR over-expression system from System Biosciences, Mountain View, Calif.), pGIPZ-miR-141 (based on pGIPZ lentiviral backbone from Open Biosystems, pGIPZ-NS as the control), and pTRIPZ-141 (based on pTRIPZ inducible lentiviral backbone from Open Biosystems, pTRIPZ-NS as the control). pGIPZ and pTRIPZ lentiviral vectors were produced in HEK293T packaging cells with Trans-Lentiviral packaging system (Open Biosystems). Lenti-miR-141 and Lenti-ctl viruses were produced in 293T packaging cells with the packaging plasmid mix as previously described (13). Titers were determined by infecting and counting the GFP+293T cells. Prostate cancer cells (from either cultures or xenografts) were infected with the lentiviral supernatant at Multiplicity of Infection (MOI) of 10-20 in the presence of 8 µl/mL polybrene and harvested 48-72 h after infection for experiments.

Clonal and Sphere Formation Assays

For clonal assays, cultured prostate cancer cells or human prostate cancer cells freshly purified from patient primary tumors were plated at a clonal density (i.e., 100 cells/well) in a 6-well plate. The number of holoclones (33) was counted several days later. For Matrigel-based sphere formation assays, cells in medium were plated (generally 1,000 cells/well) in Matrigel at 1:1 ratio in a total of 100 µl in 96-well plates. Spheres were enumerated 1-2 weeks after plating. For floating sphere formation assays, cells were plated in serum-free epithelial basal medium (PrEBM) supplemented with B27 (Invitrogen), and 20 ng/ml EGF and bFGF in ultra-low attachment (ULA) plate. Floating spheres that arose in 1-2 weeks were counted. For all these experiments, a minimum of triplicate wells was run for each condition and repeat experiments were performed when necessary and feasible.

Migration and Invasion Assays

For Boyden Chamber invasion assays, Biocoat Matrigel Invasion Chamber (BD, Franklin Lakes, N.J.) was employed following the manufacturer's instructions. Briefly, 100,000-200,000 of prostate cancer cells after transfection with neutral control/miR-141 oligos or infection with miR-141 over-expressing lentivirus were seeded into each well. Medium with 20% fetal bovine serum was used in the lower chamber as chemo-attractant. After 20 h, cells were fixed and stained using HEMA stain. Representative images were taken for each membrane and cells were counted. Migration assays were simultaneously performed in control wells using identical protocol with Transwell (Costar; 8 µl PET) without Matrigel. In some experiments, Du145 cells were plated one day before and treated with 1, 2, and 5 µM of DZNep (3-Deazaneplanocin A) for 96 h after which cells were harvested and used in invasion assays and Western blot.

EdU Flow Cytometry

EdU (5-ethynyl-2'-deoxyuridine) is a nucleoside analog to thymidine and incorporated into DNA during active DNA synthesis. EdU incorporation assays were performed using Click-iT EdU Flow Cytometer Assays kit (C10418, Invitrogen) per manufacturer's instructions. Briefly, PPC-1 bulk cells or $CD44^+$ DU145 cells transfected with negative control or miR-141 oligos (30 nM) for 48 h were pulsed with 10 µM EdU for 2.5 h and harvested. After fixation and permeabilization, cells were processed for EdU immunostaining and also labeled with Pacific Blue azide (1:200) and finally analyzed on a flow cytometer.

Luciferase Reporter Assays

The human CD44 3'-UTR was amplified from Du145 genomic DNA using primers 5'-AGAGCTCCACCTACAC-CATTATCTTG-3' (SEQ ID NO: 2) and 5'-TAAGCTTG-GAAGTCTTCAGGAGACAC-3' (SEQ ID NO: 3), as previously described (13). For site-specific mutagenesis, the region in the CD44 3'-UTR (SEQ ID NO: 4, shown with uracils) complementary to the seed sequence of miR-141 (SEQ ID NO: 1) were mutated (TAGTGTT to GGCGCGG; see FIG. 3D). The human EZH2 3'-UTR was amplified from Du145 genomic DNA using primers 5'-GAGCTC-CATCT-GCTACCTCCTCCCC-3' (SEQ ID NO: 6) and 5'-AAGCT-TGACAAGTTCAAGTATTCTTTATT-3' (SEQ ID NO: 7). For site-specific mutagenesis, the region complementary to the seed sequence of miR-141 was mutated (AAAGTGTT to TATCACAA; see FIG. 6A). The PCR fragments were cloned into pGEM-T vector (Promega, Madison, Wis.) and sequence confirmed. Cells were plated in 24-well plates and co-transfected, using Lipofectamine 2000, with 1 µg firefly luciferase reporter plasmid and 5 ng *Renilla* plasmid (phRL-CMV) into which the 3'-UTR fragments were cloned. The luciferase activities were detected using Duo-luciferase reporter assay system (Promega). Human RAC1, CDC42, CDC42EP3, and ARPC5 3'-UTR luciferase reporter constructs were obtained from SwitchGear Genomics (Menlo Park, Calif.) and luciferase activities were measured per the manufacturer's instructions using LightSwitch luciferase assay kit.

Rho Family GTPase Activity Assay

The activity of Rho family of small GTPases including RhoA, RAC1 and CDC42 were detected using G-LISA small G-protein activation assays per the manufacturer's instructions (Cytoskeleton, Inc., Denver, Colo.; catalog# BK135).

RNA-Seq, Data Processinq and Bioinformatics

Du145 and LAPC9 cells were transfected with 30 nM of miR-141 or negative control oligos for 48 h. Total RNA was purified using RNeasy mini kit (Qiagen, Hilden, Germany). The overexpression of miR-141 was validated by qPCR. 100 ng of total RNA samples was then converted to cDNA using a NuGEN Ovation RNA-Seq System v2 according to the manufacturer's protocol (NuGEN, San Carlos, Calif.). NuGEN-amplified double-stranded cDNAs were fragmented into ~180 base pair (bp) using a Covaris system (Covaris, Woburn, Mass.). Fragmented cDNAs were run on a SPRI-TE library construction system (Beckman Coulter, Fullerton, Calif.), and during the adaptor ligation step, uniquely indexed NEXTflex adapters (Bioo Scientific, Austin, Tex.) were used for each of the samples to allow for multiplexing. Adapter-ligated libraries were enriched by PCR using a KAPA library amplification kit (KAPA Biosystems, Wilmington, Mass.) (1 cycle at 98° C. for 45 seconds; 7 cycles at 98° C. for 15 seconds, 65° C. for 30 seconds, and 72° C. for 30 seconds; 1 cycle at 72° C. for 1 minute), and purified with AMPureXP beads (Beckman Coulter, Pasadena, Calif.). The purified libraries were quantified using a KAPA library quantification kit. The libraries were loaded on cBot (Illumina, San Diego, Calif.) at final concentration of 10 µM to perform cluster generation, followed by 2×76 bp sequencing on HiSeq 2000 (Illumina, San Diego, Calif.).

Sequencing reads were mapped to reference human genome sequence (NCBI 36.1 [hg19] assembly by TopHat (Version 2.0.6). The number of fragments in each known gene from RefSeq database (downloaded from UCSC Genome Browser on Mar. 9, 2012) was enumerated using htseq-count from HTSeq package (version 0.5.4p9). Genes with less than 10 fragments in all the samples were removed before differential expression analysis. The differential expression between conditions was statistically assessed by R/Bioconductor package edgeR (version 3.0.8). Genes with FDR (false discovery rate) of ≤0.05 and >200 bp were called as differentially expressed.

Figure 4A:
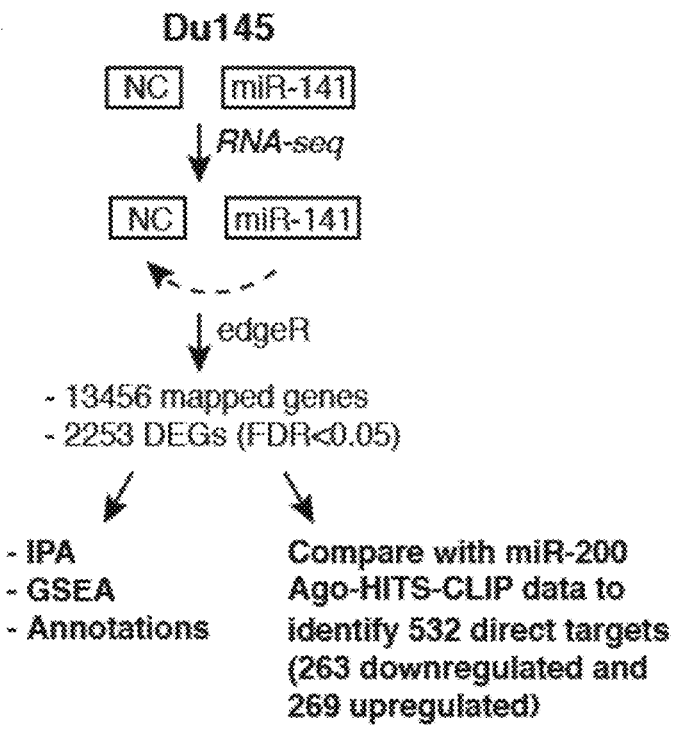
FIGS. 4A-4Y shows that RNA-Seq analysis reveals novel miR-141 targeted signaling molecules and pathways.
Figure 4B:
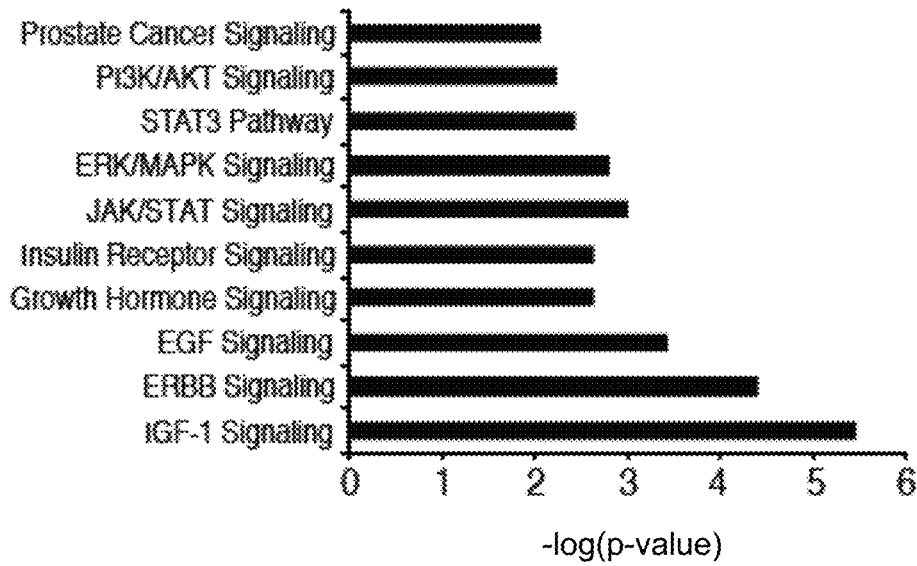
FIG. 4B shows major mitogenic pathways affected by miR-141 expression in Du145 cells revealed by IPA.
Figure 4C:
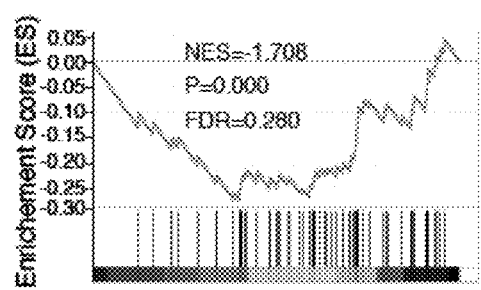
FIGS. 4C-4E shows GSEA reveals negative enrichment of miR-141-altered genes in CELL CYCLE (FIG. 4C) and ESC core (FIG. 4D) gene sets but positive association with "Mammary Stem Cell Downregulated" gene set (FIG. 4E).
Figure 4D:
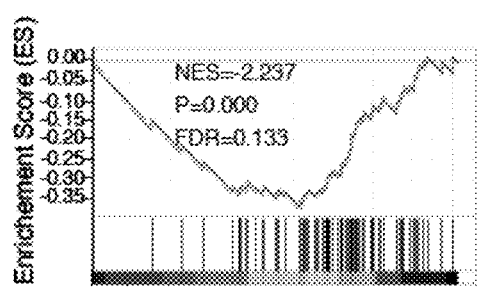
Figure 4E:
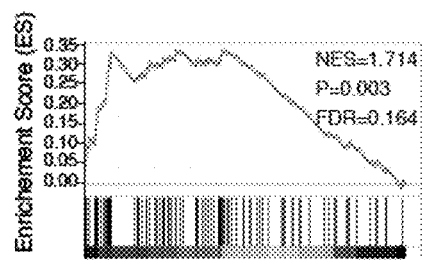

For Gene Ontology (GO) analysis, IPA (Ingenuity Pathway Analysis; Qiagen, Valencia, Calif.) and GSEA (Gene Set Enrichment Analysis; Broad Institute) were performed. The standard procedure was followed (www.broadinstitute.org/gsea/doc/GSEAUserGuideFrame.html) as described by GSEA user guide and used curated gene set C2 of the Molecular Signature Database (MSigDB) version 4.0 to compute overlaps between gene set and gene sets in MSigDB. Some of the datasets presented in the text are annotated here. For example, Wong and colleagues (63) identified a core ESC-like gene module containing genes coordinately upregulated in a compendium of mouse embryonic stem cells (ESC) that are shared with the human ESC-like module (FIG. 4D). In another study, Lim et al. identified a gene signature (FIG. 4E) that was consistently down-regulated in mammary stem cells in both mouse and human (64). Through whole-genome DNA microarrays in 31 breast cancer cell lines, Charafer-Jauffret et al. found a list of genes (FIG. 4I) that was up-regulated in luminal-like breast cancer cell lines compared to the mesenchymal-like breast cancer lines (65). Onder and colleagues (66) performed gene expression analysis in HMLE cells (immortalized nontransformed mammary epithelium) after E-cadherin (CDH1) knockdown by RNAi, and identified genes that were down-regulated after loss of E-cadherin (FIG. 4J). To analyze epithelial to mesenchymal transition-causing pathways in tumorigenesis, Aigner and colleagues (67) identified a gene signature that was up-regulated in MDA-MB-231 breast cancer cells after knockdown of ZEB1 by RNAi (FIG. 4K) representing transcriptional targets of Ecadherin repressor ZEB1 in invasive human cancer cells.

Identification of Putative Direct miR-141 Tarqets in Prostate Cancer Cells by Merging RNA-Seq Data with the miR-200a Ago-HITS-CLIP-Seq Data The authors' in-house scripts (12) was utilized for sequence alignment and peak calling. The miR-200a CLIP-Seq results containing the binding information were further extracted and merged with Du145 or LAPC9 RNA-Seq data by gene symbol.

siRNA-Mediated Knockdown siRNAs targeting RAC1, CDC42 and EZH2 were purchased from Origene (Rockville, Md.). Three unique 27mer siRNA duplexes for each target were provided. siRNAs were transfected at 10 nM for 48 h using Lipofectamine RNAiMax (Life Technologies). Knockdown efficiency was determined by qPCR.

Statistical Analyses

In general, experiments were done in triplicates for each condition when feasible. Results are presented as mean±standard deviation (STDEV) calculated using Microsoft Excel. Statistical differences were determined using unpaired two-tailed Student's t-test for most analyses except for tumor incidence for which a Chi square test was used. P-values less than 0.05 are considered statistically significant. No statistical method was used to pre-determine sample size and no samples were not excluded for any analysis.

Accession Number

The DNA and RNA sequence data was deposited with NCBI Gene Expression Omnibus under accession number GSE71756.

Example 2 miR-141 is Under-Expressed in CD44$^+$ Prostate Cancer Cells in Both Xenograft and Patient Tumors Systematic studies on prostate cancer cell heterogeneity has established that the CD44$^+$ prostate cancer cell population in multiple xenograft models as well as primary patient tumors is enriched in clonogenic and tumorigenic cells that fulfill cancer stem cell definitions (13, 20, 21, 23, 25).

Figure 1B:
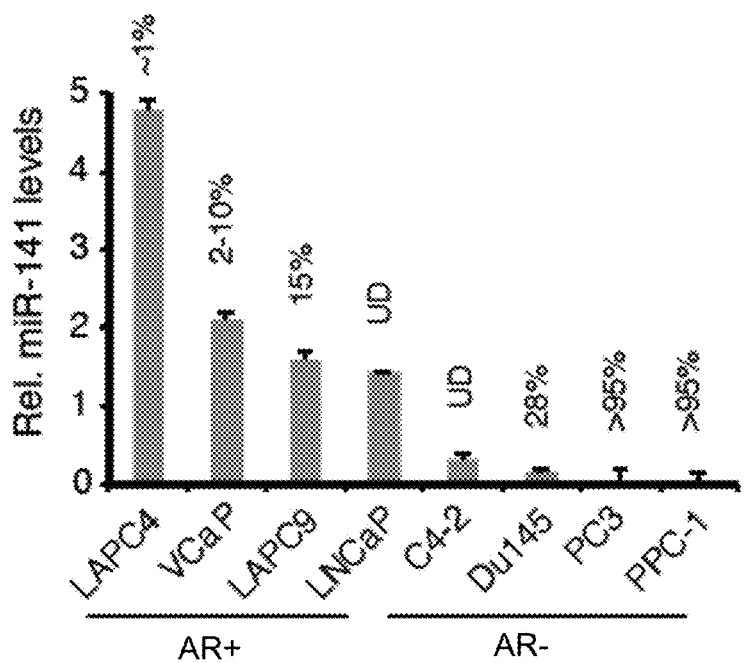
Figure 1C:
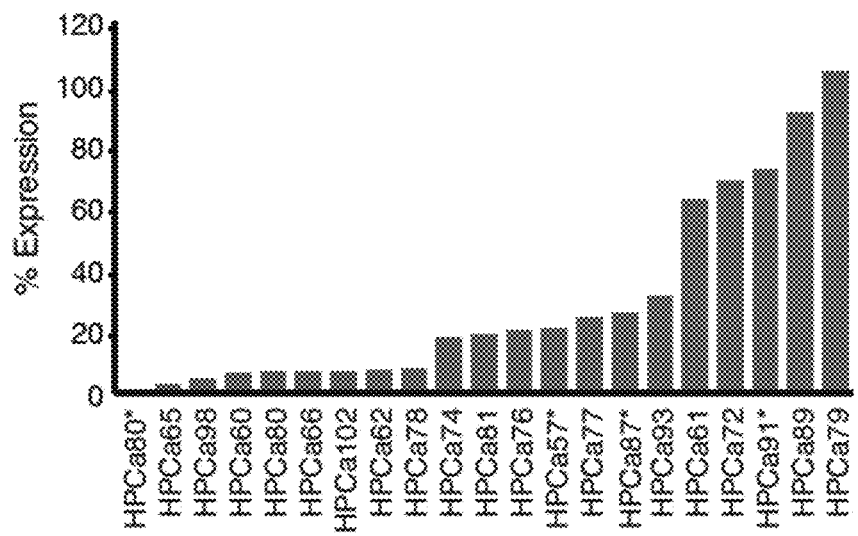

CD44$^+$ Prostate cancer cells were purified from LAPC9, LAPC4, and Du145 xenografts and VCaP cultures, and, for comparisons, CD133+ cells (19) were purified from LAPC4 xenografts, and integrin $\alpha_2\beta_1^+$ cells (21,25) from Du145 xenografts, and performed qRT-PCR analysis of mature miR-141 levels relative to the corresponding marker-negative cell populations. It was found that miR-141 was commonly underexpressed in these prostate cancer stem/progenitor populations, including all CD44$^+$ subpopulations (FIG. 1A). Furthermore, correlation analysis in 8 prostate cancer xenograft/culture derived cells revealed that the miR-141 mRNA levels overall inversely correlated with the abundance of CD44$^+$ cells in each model (FIG. 1B). Importantly, the miR-141 levels were much lower in the CD44$^+$ cells freshly purified from 21 primary human prostate cancer (HPCa) patient samples compared to the corresponding CD44⁻ human prostate cancer cells (FIG. 1C).

Figure 1D:
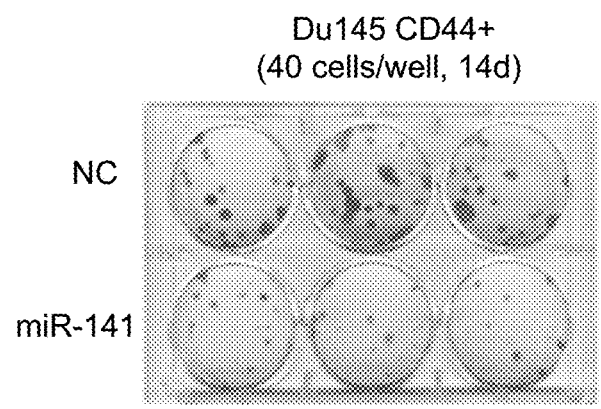
Figure 1E:
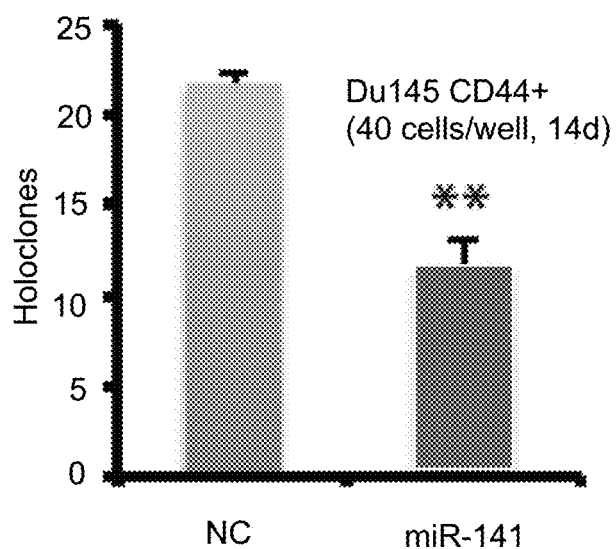
Figure 1F:
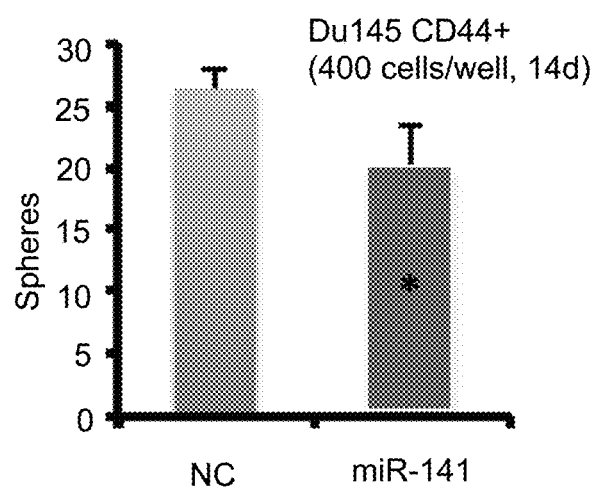
Figure 1G:
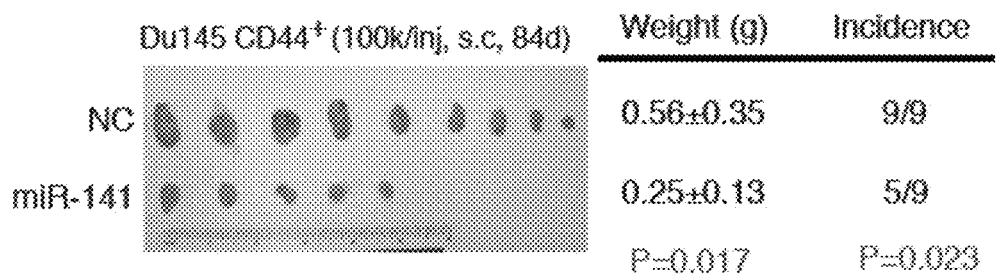
Figure 1H:
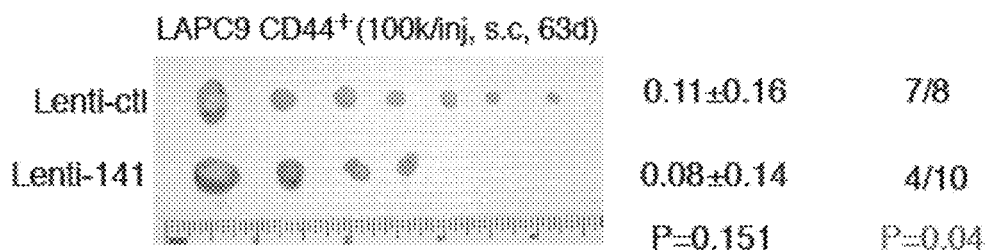
Figure 1I:
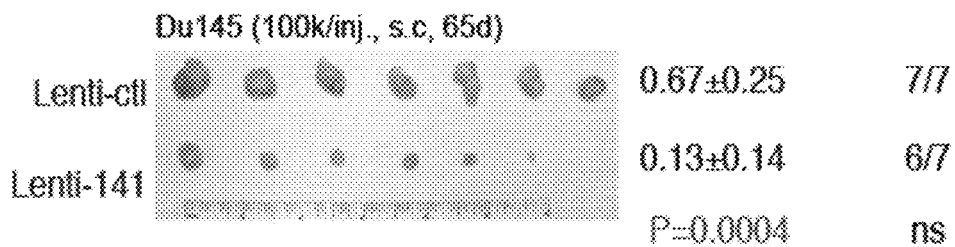
Figure 1J:
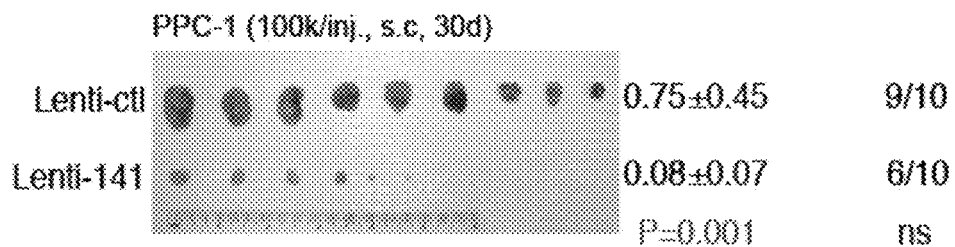
Figure 1K:
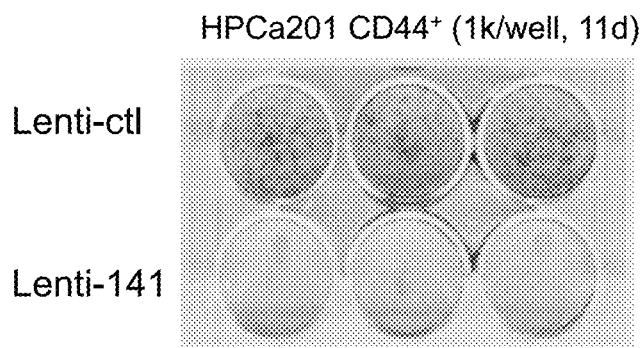
Figure 1L:
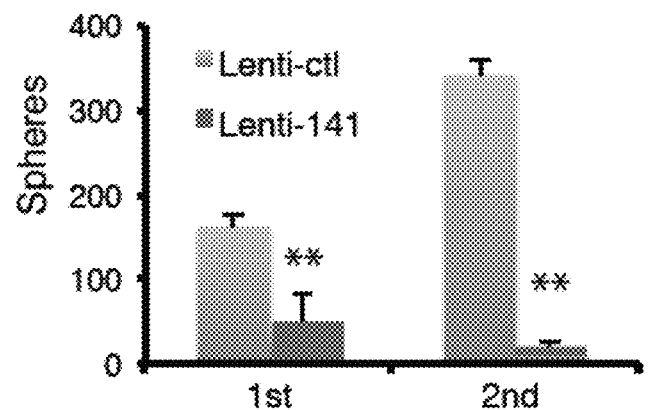
Figure 1M:
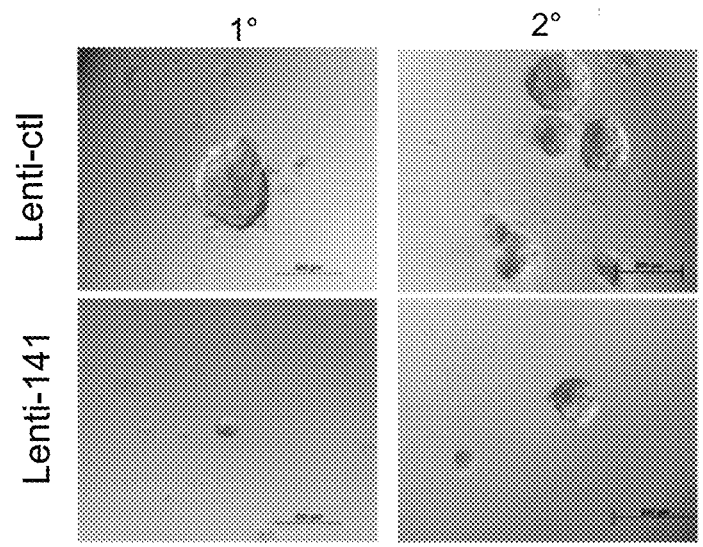

Example 3 miR-141 Over-Expression Inhibits Prostate Cancer Stem Cell Properties and Tumor Regeneration As the CD44⁺ prostate cancer cells are prominently devoid of miR-141, its expression in CD44⁺ prostate cancer cells was restored and then cancer stem cell assays including stringent clonal (holoclone) and single cell-derived sphere-formation assays (13, 14, 23, 25, 33) were performed. CD44⁺ Du145 cells were freshly purified out by FACS, transfected with the miR-141 mimicking (miR-141) or control (NC) oligos for 48 h, and then plated cells for clonal and sphere assays. miR-141 transfection, inhibited both the clonogenic (FIGS. 1D &1E) and sphere-forming (FIG. 1F) capacities of CD44⁺ Du145 cells. In vivo tumor regeneration assays was performed (FIGS. 1G-1J) in bulk or purified CD44⁺ prostate cancer cells over-expressing miR-141 via either oligo transfection or lentiviral transduction. Enforced miR-141 expression significantly suppressed tumor growth and/or reduced tumor incidence in CD44⁺ Du145 (FIG. 1G) and LAPC9 (FIG. 1H) cells. A similar trend of tumor-inhibitory effect of miR-141 on CD44⁺ VCaP cells was also observed. Importantly, over-expression of miR-141 in bulk prostate cancer cells also suppressed tumor regeneration in both Du145 (FIG. 1I) and PPC-1 (FIG. 1J) models. Consistent with its tumor-inhibitory effects, miR-141 inhibited clonal expansion and sphere formation in PPC-1 cells. miR-141 suppression of Prostate cancer clonal and tumor growth was associated with inhibition of cell proliferation as evidenced by reduced EdU incorporation in miR-141-over-expressing cells and reduced Ki-67⁺ cells in miR-141-overexpressing tumors. miR-141 expression showed minimal effects on cell death and senescence. These results, together, suggest that miR-141 possesses prostate cancer-suppressive functions via inhibiting cell-cycle progression. Of clinical relevance, miR-141 overexpression inhibited clonal growth (FIG. 1K) and serial sphere formation in CD44⁺ (FIGS. 1L-1M) and bulk human prostate cancer (HPCa) cells freshly purified from patient tumors.

Example 4 miR-141 Inhibits Prostate Cancer Metastasis and Exhibits Therapeutic Efficacy

Figure 2A:
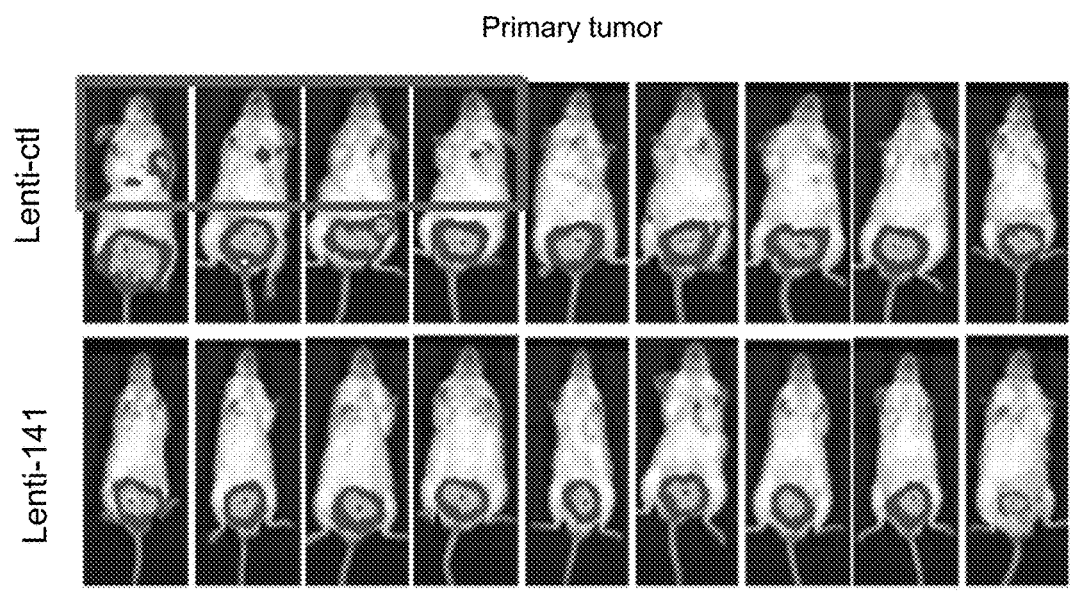
FIGS. 2A-2I show that miR-141 inhibits lung metastasis of CD44$^+$ PCa cells.
Figure 2B:
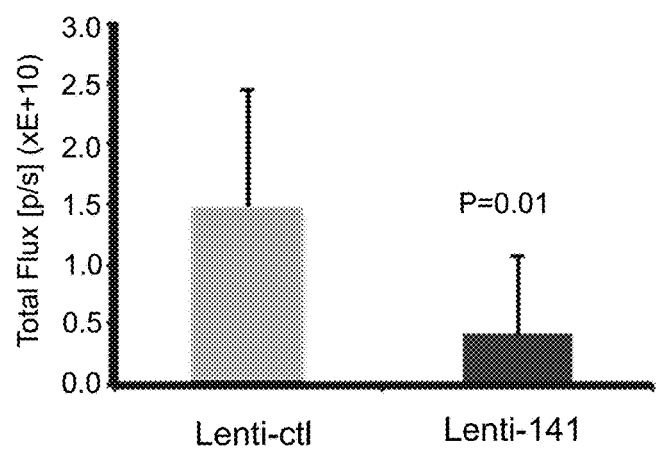
Figure 2C:
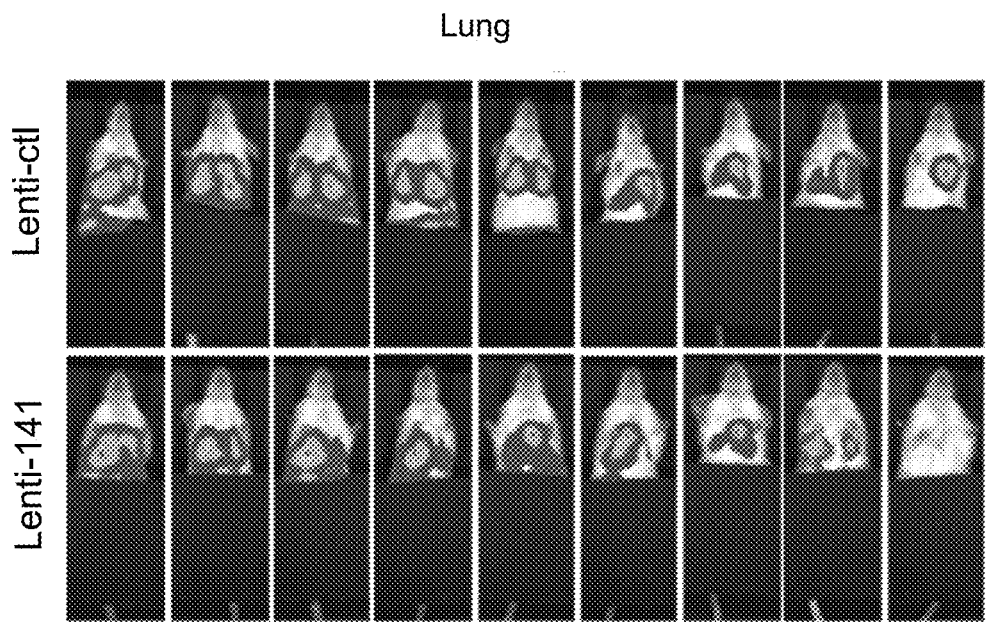
Figure 2D:
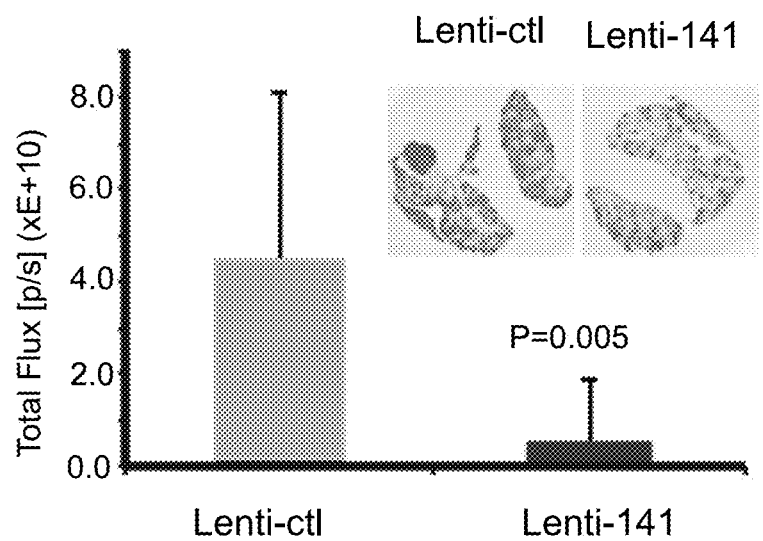
Figure 2E:
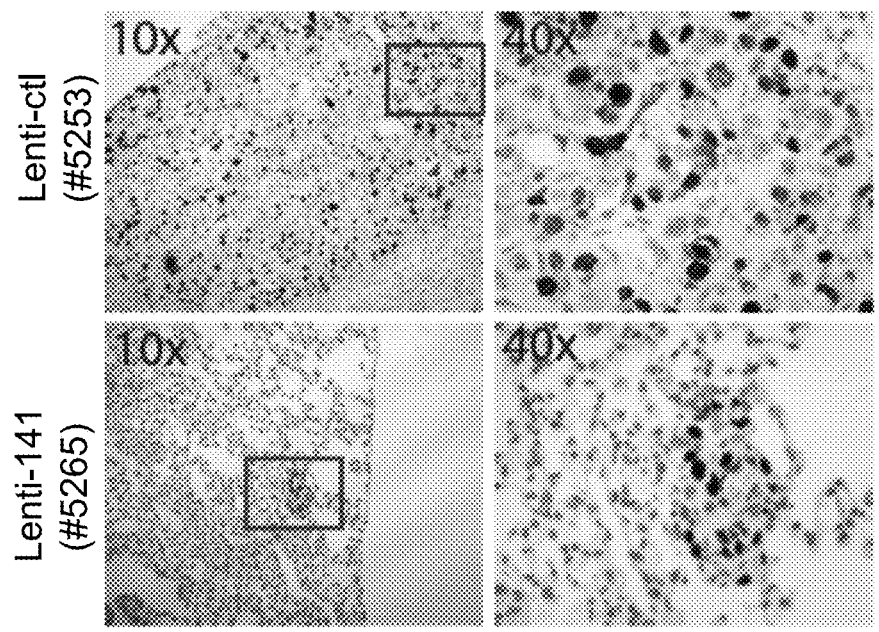
Figure 2F:
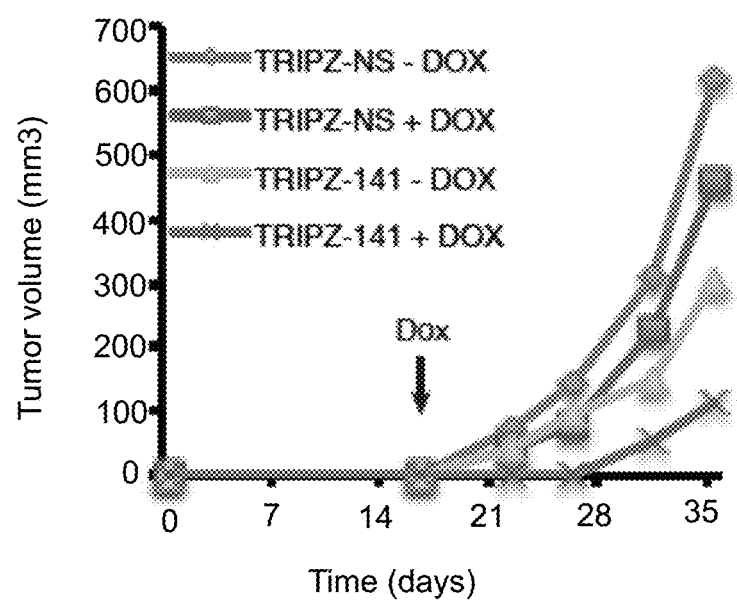
Figure 2G:
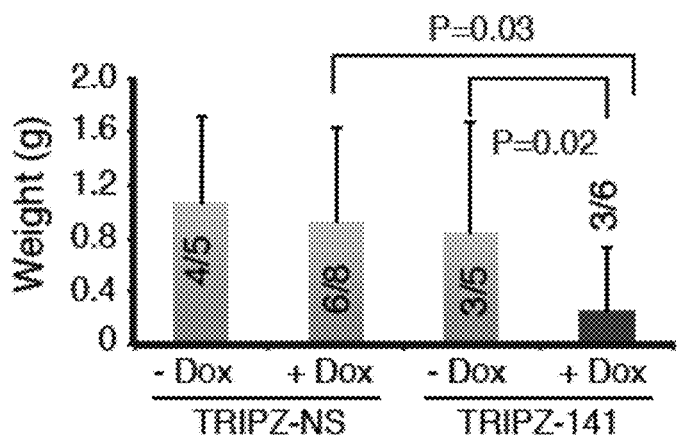
Figure 2H:
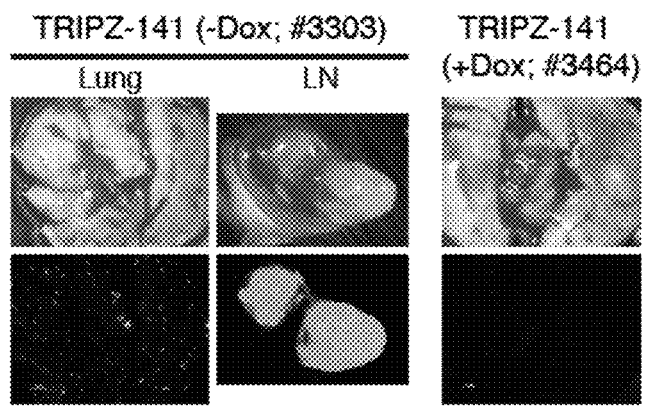
Figure 2I:
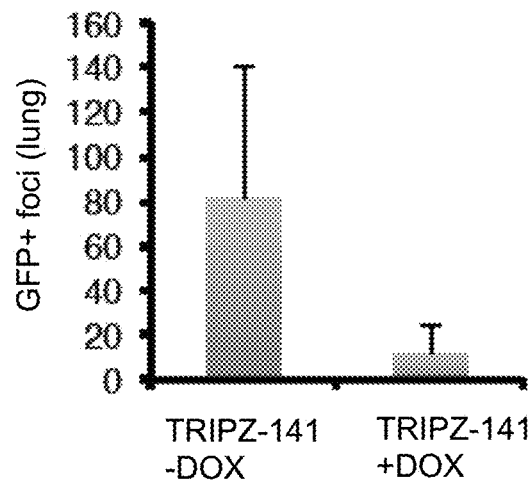

It has been demonstrated that the CD44⁺ prostate cancer cell population acutely purified from xenograft models possesses high metastatic potential (13, 20, 25). Thus, it was decided to determine if manipulating miR-141 levels in CD44⁺ or bulk prostate cancer cells would affect their metastatic capabilities. To this end, miR-141 was introduced via lentiviral infection into CD44$^{hi}$ PC3-luc cells and then implanted the cells into the dorsal prostate (DP) of NOD/SCID mice (13, 20, 25). miR-141 over-expressing CD44$^{hi}$ PC3 cells produced smaller primary tumors (FIGS. 2A & 2B) as well as less lung metastasis (FIGS. 2C-2D). The miR-141 over-expressing CD44⁺ Du145 cells were also implanted into the dorsal prostate of NOD/SCID mice and observed similar inhibitory effects of miR-141 on primary tumor growth as well as metastasis in the lungs (FIG. 2E). To test whether miR-141 might possess any 'therapeutic' efficacy, a Doxycycline (Dox) inducible miR-141 lentiviral expression system was established (pTRIPZ-141). LAPC9-GFP cells infected with pTRIPZ-141 or control vector (pTRIPZ-NS) were implanted into the dorsal prostate and allowed tumors to develop for ~2 weeks to reach palpable sizes (~2-3 mm diameter). miR-141 expression with doxycycline feed was then induced on day 16. It was observed that miR-141 induction inhibited growth of LAPC9 xenografts (FIGS. 2F-2G) and reduced lung metastasis (FIGS. 2H-2I).

Example 5 miR-141 Inhibits Prostate Cancer Cell Invasion and CD44 Functions as a Direct Target of miR141

Figure 3A:
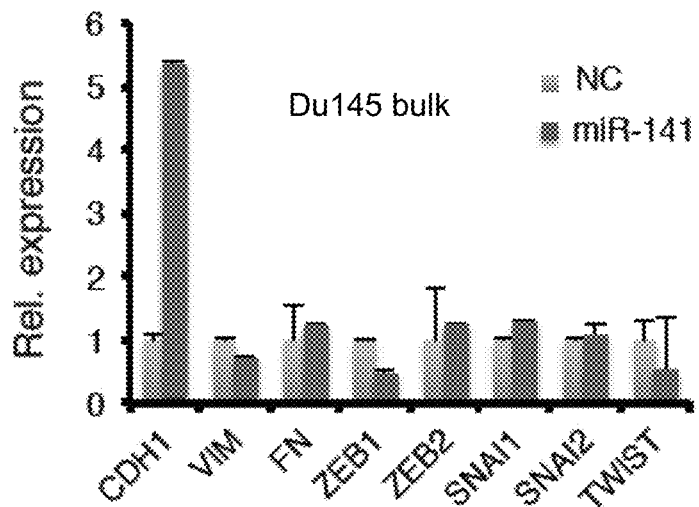
FIGS. 3A-3J show partial suppression of epithelial to mesenchymal transition by miR-141 and CD44 as a direct target of miR-141.
Figure 3B:
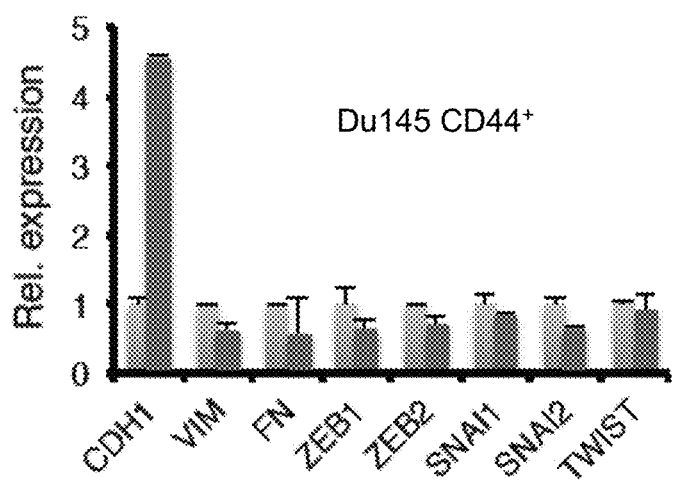
Figure 3C:
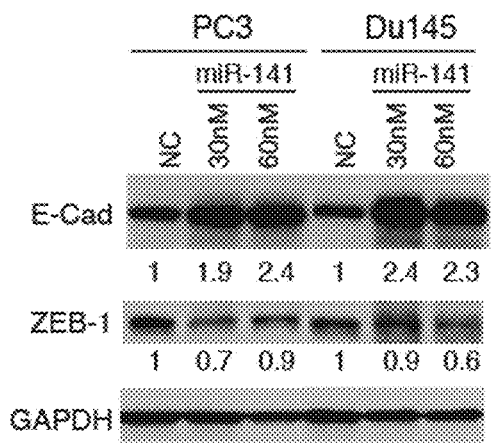

To determine molecular mechanisms underlying the metastasis-suppressing effects of miR-141 in prostate cancer cells, Matrigel invasion assays was performed, which revealed that miR-141 significantly inhibited invasive capabilities of cultured as well as primary patient human prostate cancer cells. The miR-200 family members, including miR-141, are well-established negative regulators of epithelial to mesenchymal transition (7-10). As enforced miR-141 expression inhibits prostate cancer cell invasion and metastasis, whether miR-141 exerts its effects by suppressing epithelial to mesenchymal transition (FIGS. 3A-3C) was examined. It was found that miR-141 expression in CD44⁺ Du145 cells caused significant increase in E-cadherin (CDH1) and generally reduced mRNA levels of mesenchymal markers including VIM and ZEB1 (FIG. 3B). In bulk Du145 cells, miR-141 overexpression also led to increased E-cadherin and decreased VIM and ZEB1 (FIG. 3A). Consistently, miR-141 increased E-cadherin (CDH1) and reduced ZEB1 protein levels in bulk Du145 and PC3 cells (FIG. 3C). Interestingly, however, qPCR analysis showed that in bulk Du145 cells, miR-141 did not reduce the mRNA levels of most other epithelial to mesenchymal transition markers examined including FN, ZEB2, SNAI1, SNAI2, and TWIST (FIG. 3A). These latter observations suggest that miR-141 might be inducing a 'partial' MET phenotype (27, 28, 34-36) in prostate cancer cells in that it induces a strong epithelial phenotype (evidenced by increased CDH1) but only a partial loss of mesenchymal genes.

Recent studies have suggested that cancer stem cells may not always be associated with a complete mesenchymal phenotype—rather, cancer cells with a partial epithelial to mesenchymal transition phenotype that allows a great proliferative capability of epithelial cells and the morphological plasticity of mesenchymal cells will have the best chance to survive and establish a tumor or metastatic colony (36-38). Consistent with this notion, it was observed that CD44⁺ prostate cancer/human prostate cancer cells, although possessing high tumor-regenerating and metastatic potentials (13, 20, 21, 23, 25), did not manifest a 'pure' mesenchymal gene expression profile.

Figure 3D:
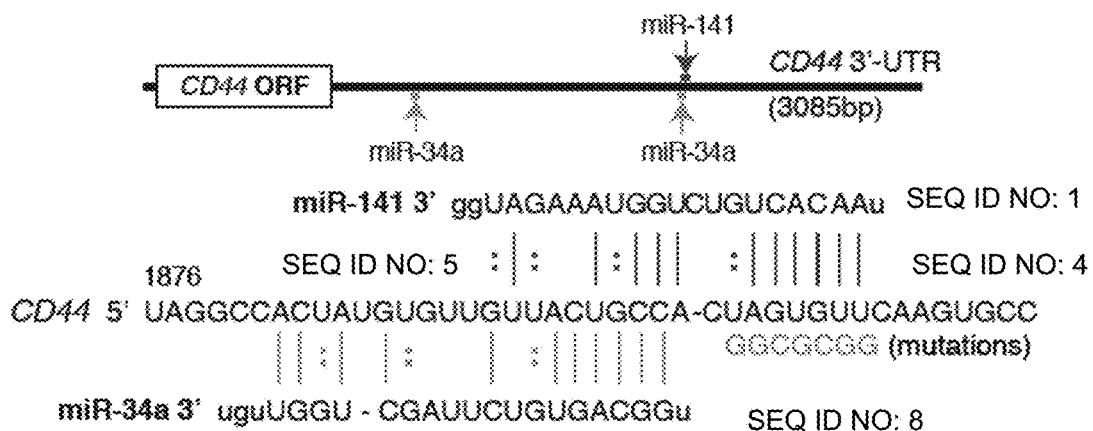
Figure 3E:
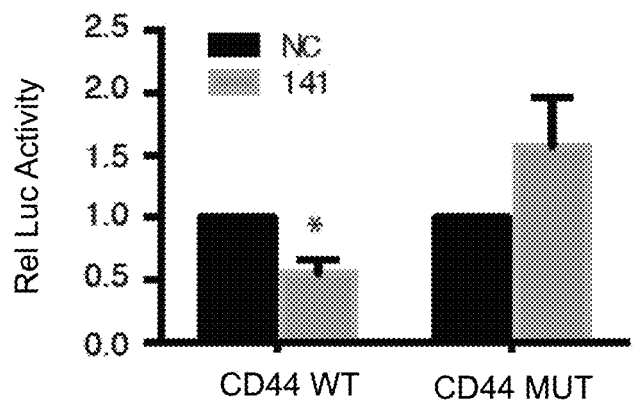
Figure 3F:
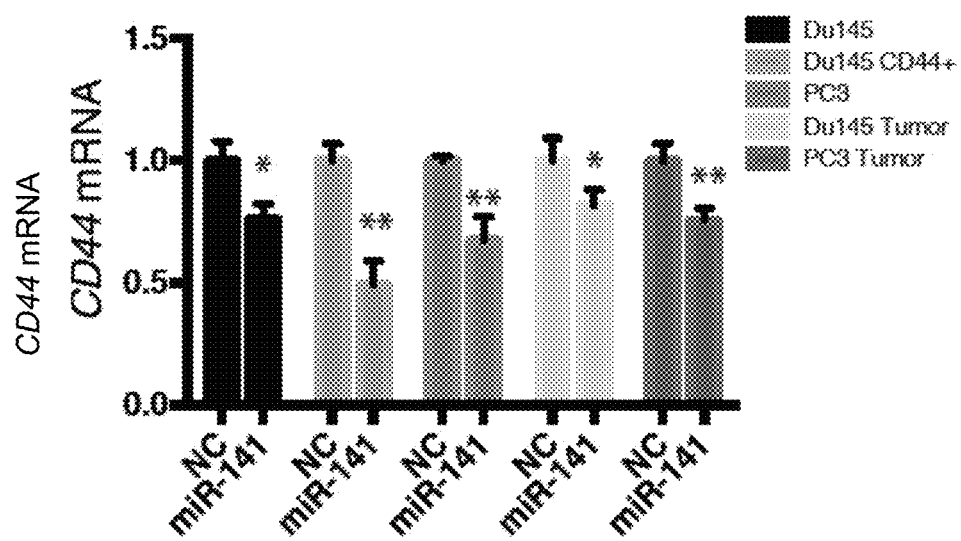
Figure 3G:
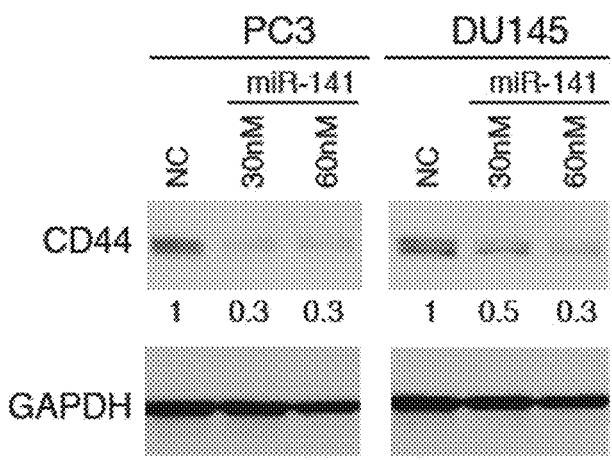
Figure 3H:
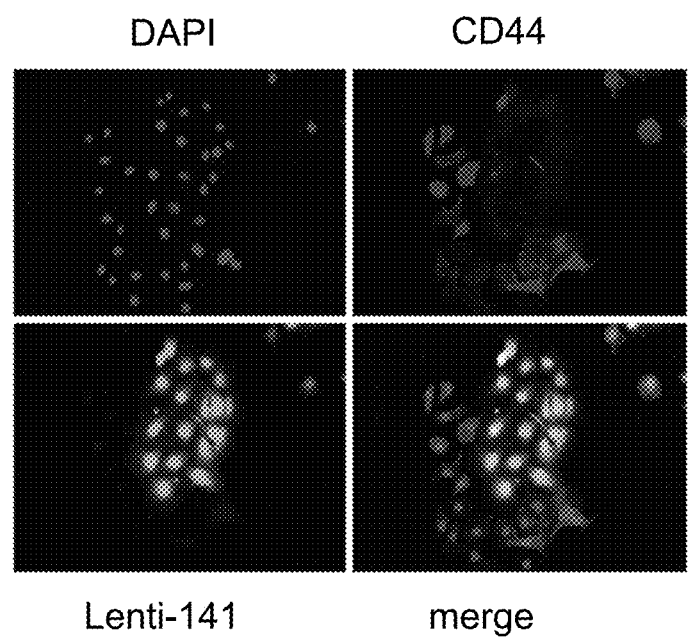
Figure 3I:
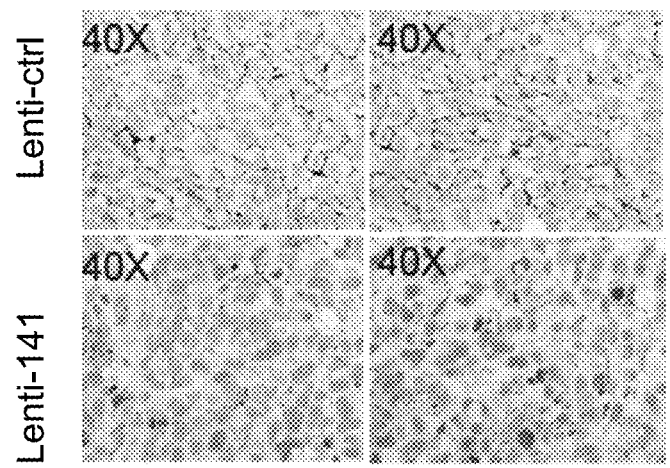
Figure 3J:
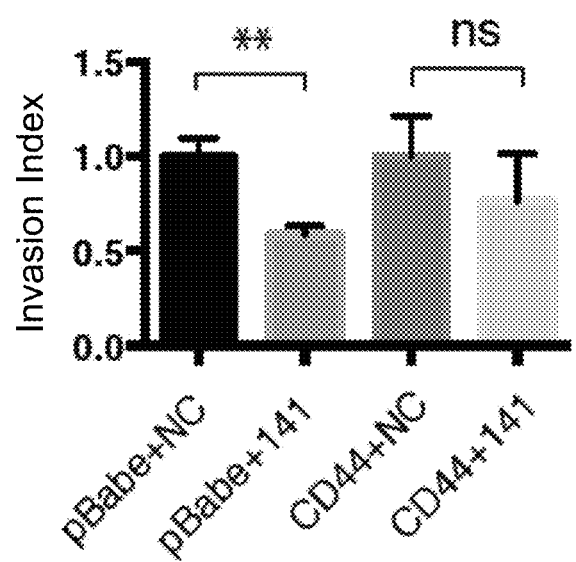

In a previous study (13), miR-34a (SEQ ID NO: 8), which was under-expressed in CD44⁺ prostate cancer/human prostate cancer cells, was found to directly target CD44 mRNA (SEQ ID NO: 5) at two sites of the 3'-UTR (FIG. 3D). Since miR-141 was also under-expressed in CD44⁺ prostate cancer (FIG. 1A) and human prostate cancer (FIG. 1C) cells and there was a good inverse correlation between % CD44⁺ prostate cancer cells and relative miR-141 levels (FIG. 1B), it was suspected that miR-141 might also target CD44. Indeed, several microRNA target prediction programs identified a putative miR-141 binding site in the 3-'UTR of CD44 that partially overlapped with and sat just slightly downstream of the second miR-34a binding site (FIG. 3D). Luciferase assays indicated that co-transfection of the luciferase reporter and miR-141 oligos into Du145 cells produced lower luciferase activities than cells co-transfected with the reporter construct plus negative control oligos (FIG. 3E). Mutation of the miR-141 binding sequence abrogated the suppressive effect of miR-141 (FIG. 3E). Over-expression of miR-141 in bulk Du145 and PC3 cells or in CD44+ Du145 cells significantly reduced CD44 mRNA and protein levels (FIGS. 3F-3G). Immunofluorescence staining for CD44 in PC3 cells that had been transduced with Lenti-141 revealed a stunning contrasting pattern such that the miR-141-expressing (i.e., GFP+) cells were largely devoid of CD44 expression (FIG. 3H). It was also found that the endpoint tumors derived from miR-141 overexpressing prostate cancer cells expressed lower levels of CD44 mRNA (FIG. 3F) and protein (FIG. 3I) than the control tumors. Finally, functional 'rescue' invasion assays was performed by overexpressing a CD44 cDNA (13) lacking the miR-141 target site. As shown in FIG. 3J, miR-141 oligo transfection inhibited Du145 cell invasion, which was partially overcome by expressing exogenous CD44. Altogether, these studies (FIG. 3D-3J) identify CD44 as a direct target of miR-141 in prostate cancer cells.

Example 6

Whole-Genome RNA-Seq Analysis Reveals Novel Pathways Regulated by miR-141

To elucidate the miR-141-regulated global gene expression changes and to identify novel targets of miR-141, genome-wide RNA-Seq was performed in Du145 (FIGS. 4A-4L) and LAPC9 (FIGS. 4M-4Y) cells transfected with miR-141 and negative control oligos. Of the 13,456 mapped genes in Du145 cells, 2,253 differentially expressed genes were identified (DEGs; FDR<0.05) including 949 down- and 1,304 up-regulated genes (FIG. 4A). Ingenuity pathway analysis (IPA) in the 2,253 DEGs revealed "Prostate Cancer Signaling" and several growth factor signaling pathways, including PI3K/AKT, ERK/MAPK, IGF-1/insulin receptor, EGF/ERBB, and growth hormone signaling, among the pathways most significantly affected by miR-141 (FIG. 4B). These latter findings suggest that miR-141 may dampen mitogenic signaling to inhibit cell-cycle progression.

Consistent with these findings, Gene Set Enrichment Analysis (GSEA) revealed that the miR-141 gene expression profile was negatively associated with the kegg reactome "cell cycle" (FIG. 4C) and "cell mitotic" terms. In addition, the miR-141 differentially expressed genes were enriched in STAT3 and JAK/Stat3 signaling (FIG. 4B), a wellknown regulator of stem cells, suggesting that miR-141 may negatively impact (cancer) stem cell signaling in Du145 cells. Gene Set Enrichment Analysis also demonstrated that the miR-141 induced gene expression changes negatively correlated with ESC core genes (FIG. 4D) and positively correlated with "Mammary Stem Cell Downregulated" (FIG. 4E). Together, these analyses indicate that miR-141 targets genes that normally promote cell cycle progression and stem cell activities, consistent with the preceding biological studies.

Figure 4F:
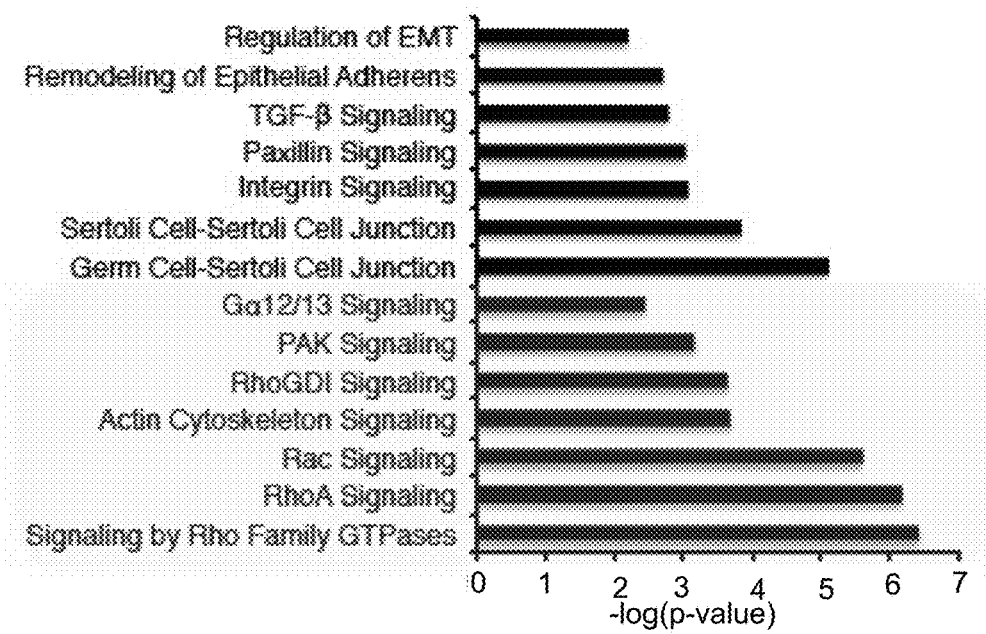
FIG. 4F shows IPA showing that miR-141 impacted several pathways involved in epithelial to mesenchymal transition and Rho family GTPase signaling (shaded).
Figure 4G:
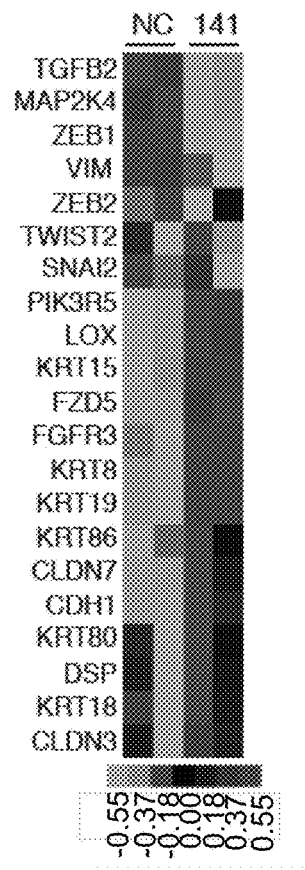
FIG. 4G shows a heat map of representative epithelial to mesenchymal transition-related molecules from Du145 RNA-Seq results.
Figure 4H:
FIG. 4H shows functional classification of the 949 genes downregulated by miR-141 in Du145 cells. The non-redundant functional classification was conducted as previously described (23, 25, 39). The % for most functional categories are indicated.
Figure 4I:
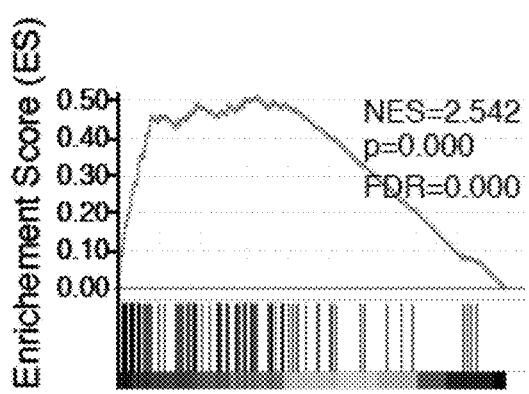
FIGS. 4I-4K shows GSEA reveals positive enrichment of miR-141-altered genes in luminal (i.e., differentiated epithelial) breast cancer cells (FIG. 4I), CDH1 targets downregulated (FIG. 4J), and ZEB1 targets (FIG. 4K) gene sets.
Figure 4J:
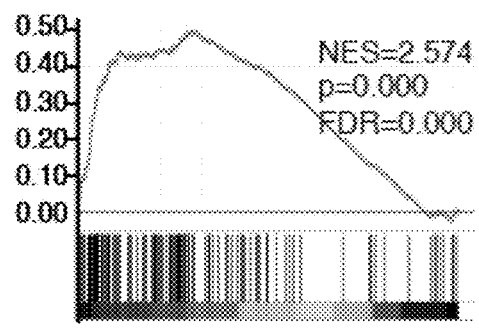
Figure 4K:
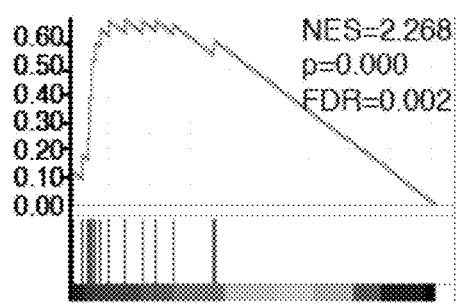
Figure 4L:
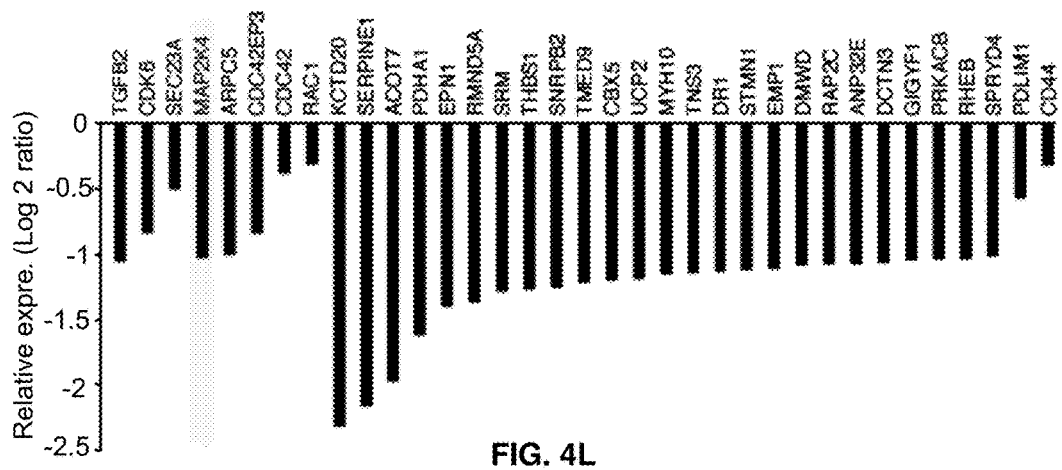
FIG. 4L shows the top 35 putative direct targets of miR-141 as revealed by merging Du145 RNA-Seq data with the miR-200 Ago-HITS-CLIP-Seq data12. Bars represent the relative expression levels of each gene from RNA-Seq.

RNA-Seq data also provided strong support to the earlier observations that miR-141 inhibits prostate cancer cell invasion and metastasis (FIGS. 4F-4K). For instance, functional annotations (23, 25, 39) of the miR-141 downregulated 949 genes in Du145 cells revealed "invasion/metastasis" and "cell cycle" to be the two major classes of the affected genes (FIG. 4H). Furthermore, consistent with well-established regulation of epithelial to mesenchymal transition by miR-200 family (7-10), miR-141 caused changes in genes involved in epithelial to mesenchymal transition, TGF-β, cell-cell junction and cytoskeleton, and other related signaling processes (FIG. 4F). Many epithelial markers including E-Cadherin, Claudin family members (e.g., CLDN7 and CLDN3), and cytokeratins (KRT) were strongly induced by miR-141 (FIG. 4G). Gene Set Enrichment Analysis also showed that the miR-141 gene expression profile was strongly enriched in the normal prostatic luminal epithelial cells recently reported (39). Meanwhile, miR-141 downregulated TGFB2, ZEB1, MAP2K4, and VIM but caused inconsistent changes in ZEB2, TWIST2, and SANI2 (FIG. 4G). These results, collectively, indicate, again, that miR-141 induces, in prostate cancer cells, a strong epithelial phenotype but only a partial loss of mesenchymal gene expression, i.e., a partial epithelial to mesenchymal transition, as supported by Gene Set Enrichment Analysis (FIGS. 4I-4K). Strikingly, among the miR-141 downregulated genes, a strong over-representation of genes associated with cytoskeleton remodeling and cell motility including Rho family GTPases was observed as well as its upstream regulators and downstream effectors (FIG. 4F). A recent study using Ago-HITS-CLIP approach identified a predominant role of the miR-200 family targets in the coordinated control of actin cytoskeleton dynamics (12). Since the miR-200 family members share largely overlapping downstream targets (8-10), the CLIP-Seq data that provided direct target association information of miR-200a, which shares identical seed sequence with miR-141 was compared with the RNA-seq data to identify direct targets of miR-141 in prostate cancer cells. From the 2,253 DEGs, 532 transcripts (263 down- and 269 upregulated) were found to have binding sites to miR-200a/miR-141 (FIGS. 4A and 4M-4T). Among the top 35 downregulated 'direct' target genes were 4 known miR-141 targets (i.e., TGFB2, CDK6, SEC23A and MAP2K4), 5 genes involved in Rho GTPase signaling (MAP2K4, ARPC5, CDC42EP3, CDC42 and RAC1), and CD44 (FIGS. 4L-4T).

Figure 4M:
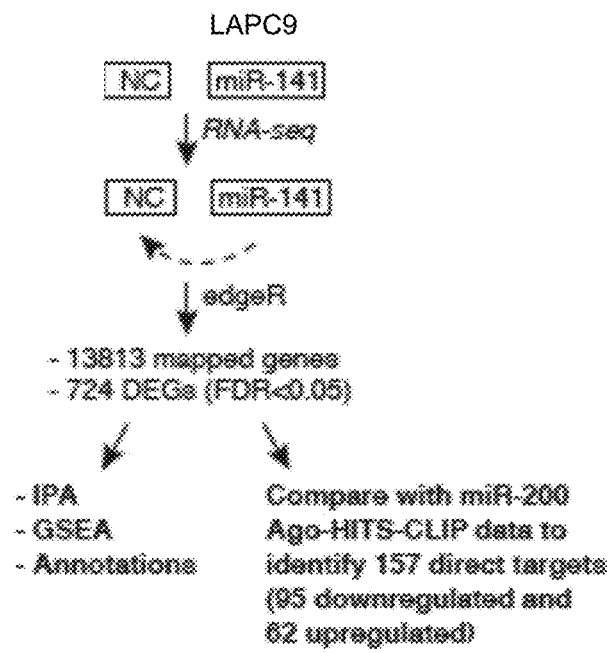
FIG. 4M shows experimental scheme of RNA-Seq in LAPC9 cells and subsequent data analysis.
Figure 4N:
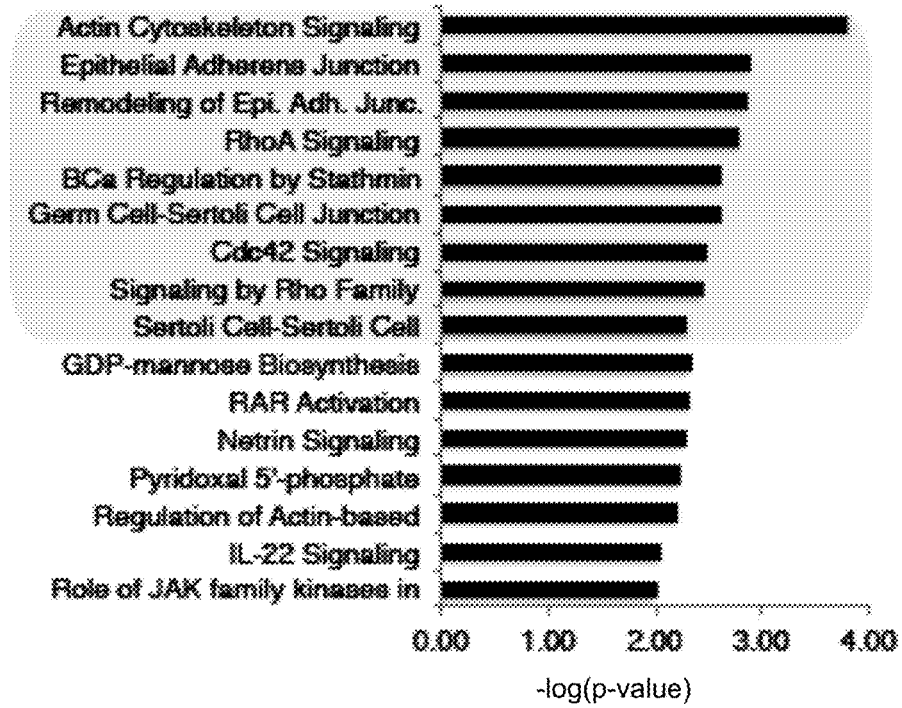
FIG. 4N shows that IPA revealed that miR-141 impacted pathways involving Rho GTPases, and actin cytoskeleton, cell-cell junction, and EMT signaling.
Figure 4O:
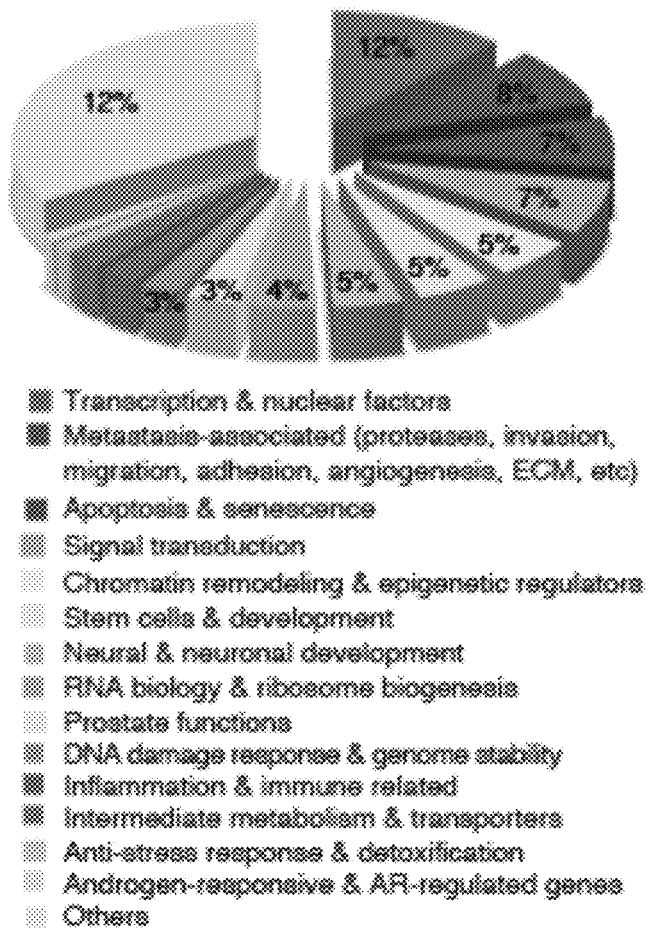
FIG. 4O shows functional classification of the 459 genes downregulated by miR-141 in LAPC9 cells. Note that the gene category classified as the "Metastasis-associated" represents one of the largest affected by miR-141.
Figure 4P:
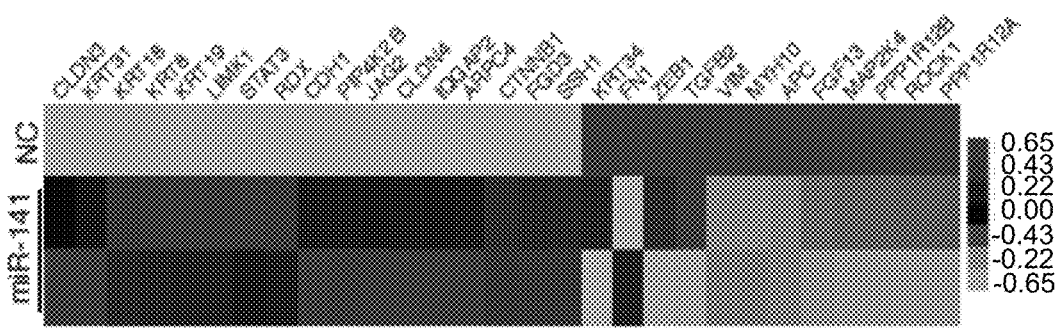
FIG. 4P is a heat map of representative EMT-related molecules in the LAPC9 RNA-Seq experiment.
Figure 4Q:
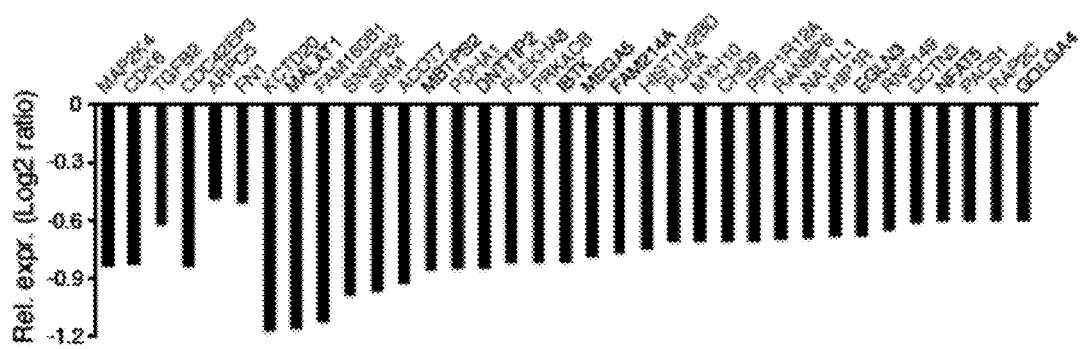
FIG. 4Q shows that the top 35 putative direct targets of miR-141 as revealed by merging LAPC9 RNA-Seq data with the miR-200 Ago-HITS-CLIP data. Bars represent the relative expression levels of each gene from RNA-Seq. Targets that are shared with the putative direct targets in Du145 cells are colored in red.

Of the 13,813 mapped genes in LAPC9, 724 DEGs (FDR<0.05) were identified including 459 down- and 265 up-regulated genes (FIG. 4M). An RNA-Seq experiment in xenograft LAPC9 cells overexpressing miR-141 also revealed that functional annotations of the 459 downregulated genes revealed "Metastasis-associated" gene category to be a major class affected by miR-141 (FIG. 4O). Similar to in Du145 cells, IPA demonstrated that miR-141 expression in LAPC9 cells impacted multiple pathways involved in actin cytoskeleton, adherens junction, and Cdc42/RhoA signaling (FIG. 4N). Furthermore, miR-141 prominently upregulated many epithelial markers including E-Cadherin, Claudin members and KRTs while downregulated TGFB2, ZEB1, MAP2K4, VIM, NYH10, FN1 and many other mesenchymal genes (FIG. 4P). GSEA positively correlated the miR-141 induced gene expression profile in LAPC9 cells with those in luminal (i.e., differentiated epithelial) breast cancer cells.

Figure 4R:
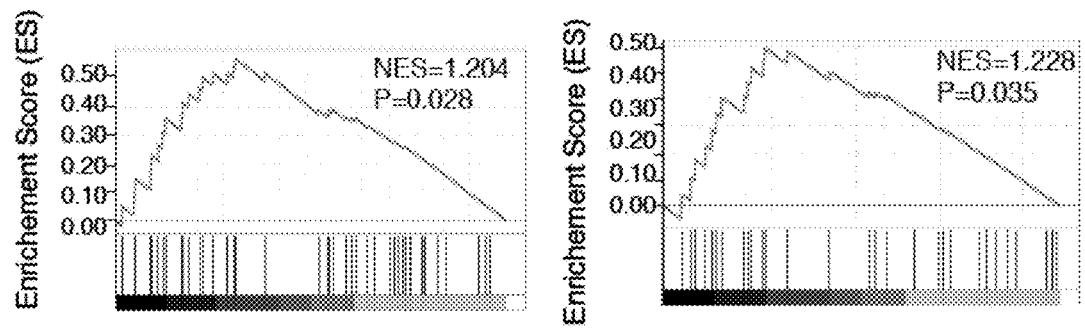
FIG. 4R shows that two "EZH2 Targets Downregulated" (DN) gene sets positively correlated with the miR-141 expressing LAPC9 gene expression profile.
Figure 4S:
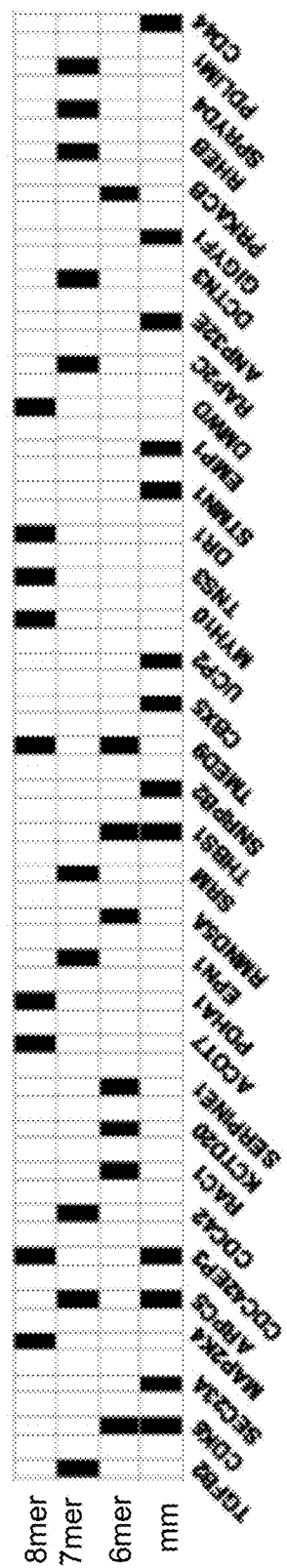
FIG. 4S shows the open reading frame. The TGFB2 mRNA has one perfectly matched 7mer binding site for miR-141 (a) whereas the CDK6 3'-UTR harbors 5 perfectly matched 6mer binding sites and 1 mismatched 8mer binding site. ARPC5 has one perfectly matched 7mer binding site and three binding sites with a mismatch in each site at the 3'-UTR. Similarly, CDC42EP3 has one perfectly matched 8mer binding site at the 3'UTR and one binding site with a mismatch in the ORF. In contrast, CDC42 (a, e), RAC1 (a, f), and PDHA1 (a, g) each has one perfectly matched 7mer, 6mer, and 8mer binding site at their respective 3'-UTR's. Finally, for CD44 (a), there is one 7mer miR-141 binding site at the 3'-UTR that contains a mismatch and 6 other potential binding sites with a mismatch in each at the 3'-UTR or ORF.
Figure 4T:
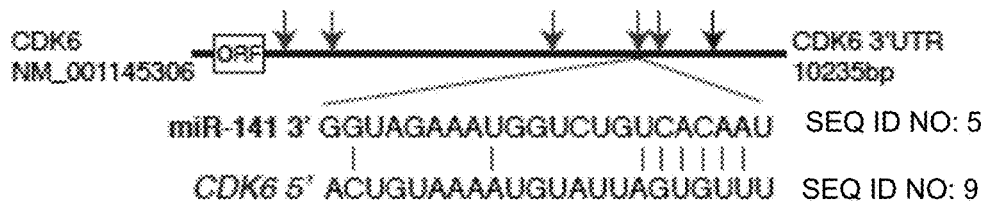
Figure 4U:
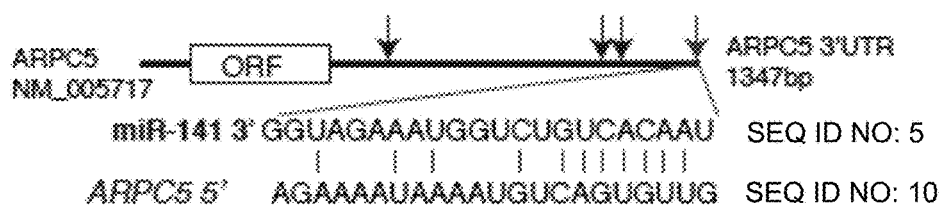
Figure 4V:
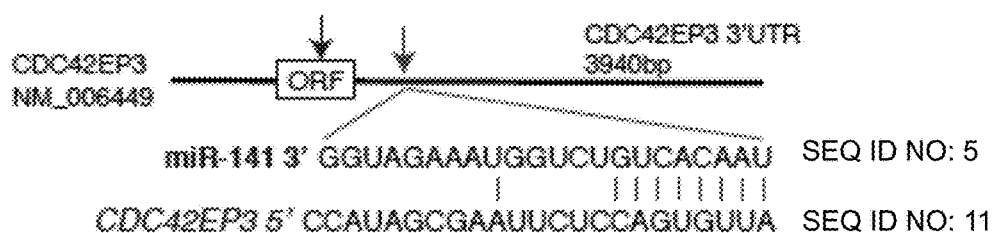
Figure 4W:
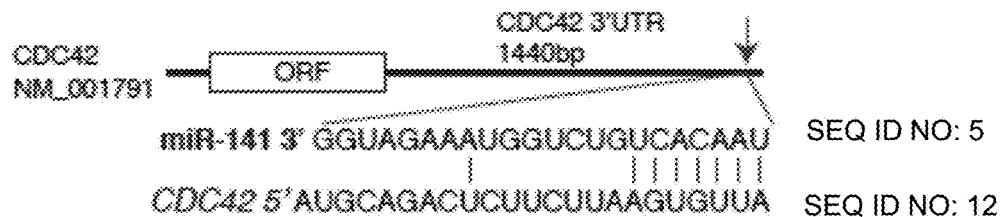
Figure 4X:
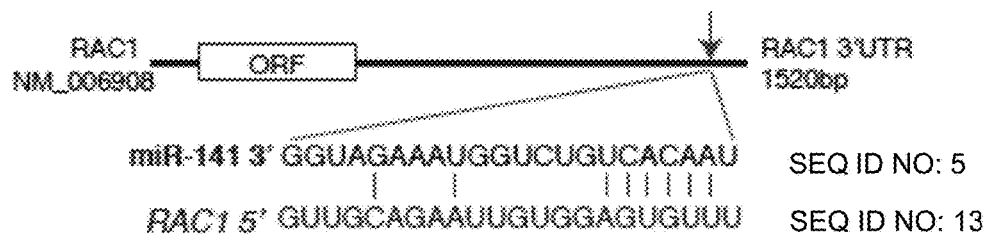
Figure 4Y:
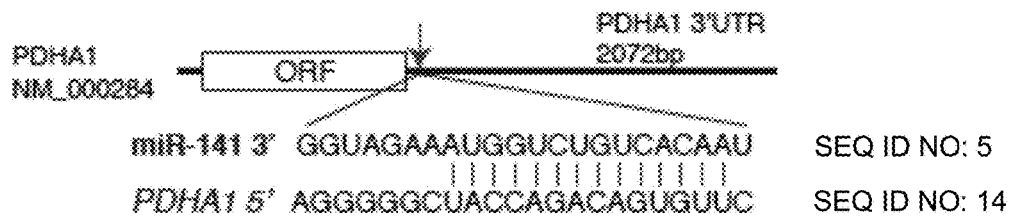

LAPC9 RNA-Seq data was then merged with the miR-200a CLIP-Seq data and found 157 putative direct targets of miR-141 in LAPC9 cells (FIG. 4M). Remarkably, 26 of the top 35 downregulated genes, including CDK6 (SEQ ID NO: 9), CDC42EP3 (SEQ ID NO: 11), and PADH1 (SEQ ID NO: 14) that harbor the miR-141 binding site(s) were commonly found in Du145 cells (FIGS. 4Q & 4S-4Y). Finally, it was found that the miR-141-induced gene expression profile in LAPC9 cells was associated with two data sets of "EZH2 Targets Downregulated" (FIG. 4R). Overall, miR-141 in LAPC9 cells elicits very similar gene expression changes and prominently targets genes involved in Rho GTPases, actin dynamics, EMT, and metastasis.

An RNA-Seq experiment in xenograft LAPC9 cells overexpressing miR-141 also revealed that: 1) miR-141 significantly downregulated metastasis-associated genes, 2) miR-141 impacted actin cytoskeleton and Rho GTPase signaling, 3) miR-141 upregulated CDH1 and many epithelial genes while downregulated numerous mesenchymal genes, and 4) miR-141 directly targeted ~150 genes, many of which were shared with the predicted targets in Du145 cells (FIGS. 4S-4Y).

Example 7

Rho GTPase Signaling Components as Direct and Functional Tarqets of miR-141

The Rho family of small GTPases plays critical roles in regulating actin dynamics, organelle development, cytoskeletal remodeling, cell movement and other cellular functions (40-42). Three major Rho GTPases, RhoA, RAC1, and CDC42, regulate different yet intertwined aspects of cell movement: RhoA mainly modulates (actin) stress fiber (and focal adhesion) formation and RAC1 mainly regulates lamellipodia formation via ARP2/3 complex whereas CDC42 is not only a major inducer of filopodia but also can activate ARP2/3 complex to form invadosomes. ARPC5 encodes one of the seven subunits of human ARP2/3 complex, which is major component of the actin cytoskeleton and can be found at the leading edge of motile cells. CDC42EP3 encodes the effector protein downstream of CDC42, which is involved in actin cytoskeleton re-organization during cell shape changes including pseudopodia formation. As the RNA-Seq analysis implicated ARPC5, CDC42EP3, CDC42, and RAC1 as direct downstream targets of miR-141 in prostate cancer cells (FIGS. 4M-4T), Western blotting analysis was performed to determine the impact of miR-141 on the protein levels of these 4 molecules.

Figure 5A:
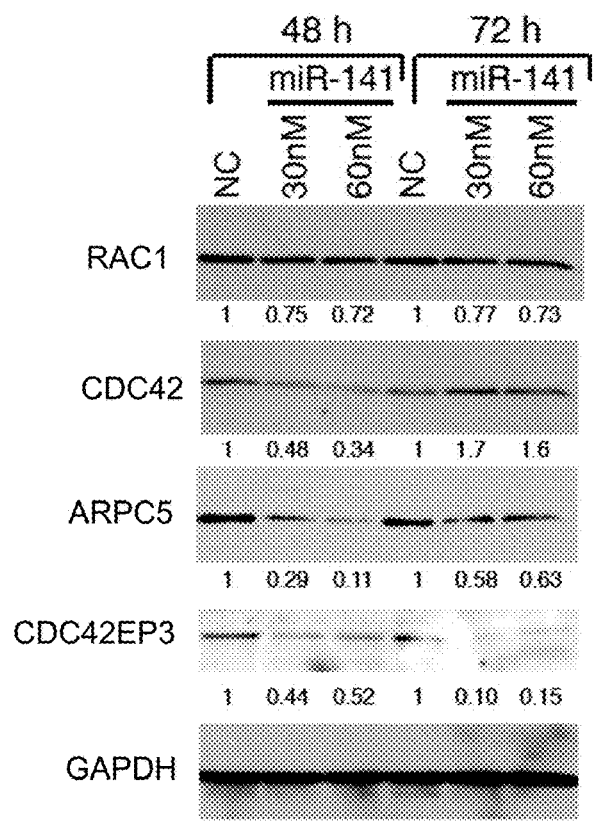
FIGS. 5A-5G shows that Rho GTPase signaling pathway members are direct targets of miR-141.
Figure 5B:
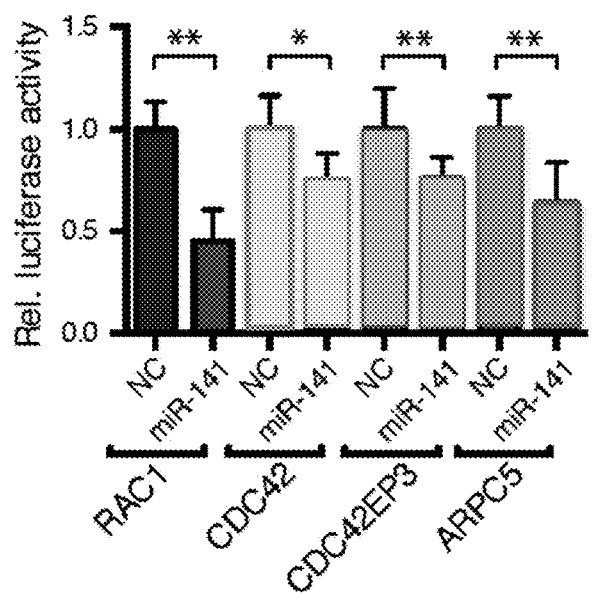
Figure 5C:
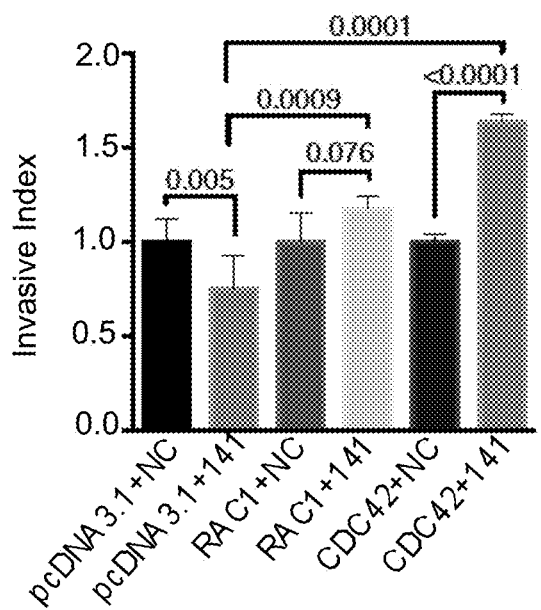
Figure 5D:
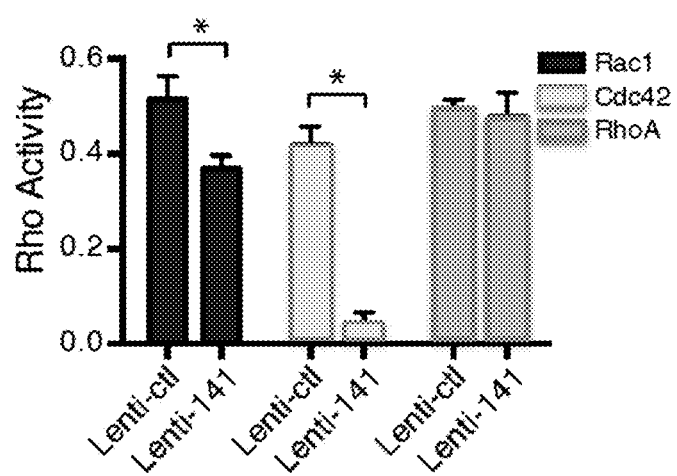
Figure 5E:
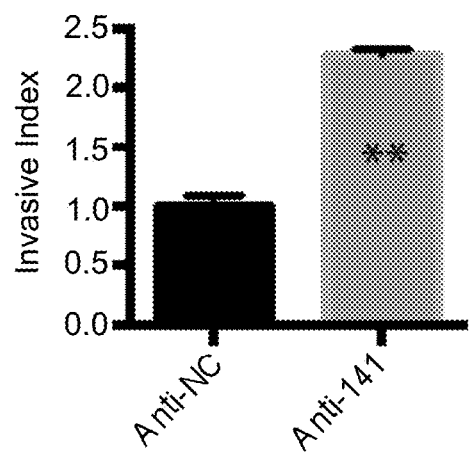
Figure 5F:
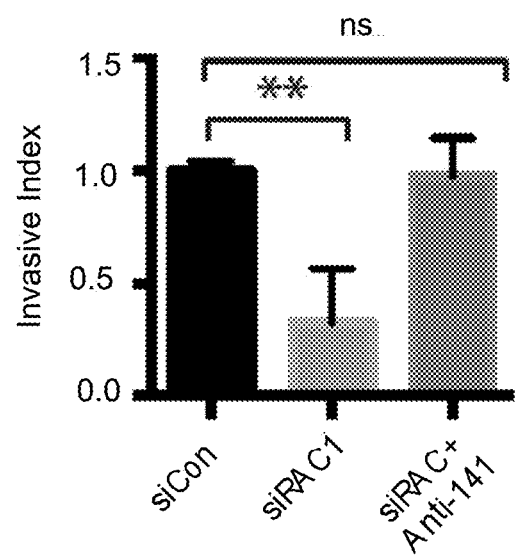
Figure 5G:
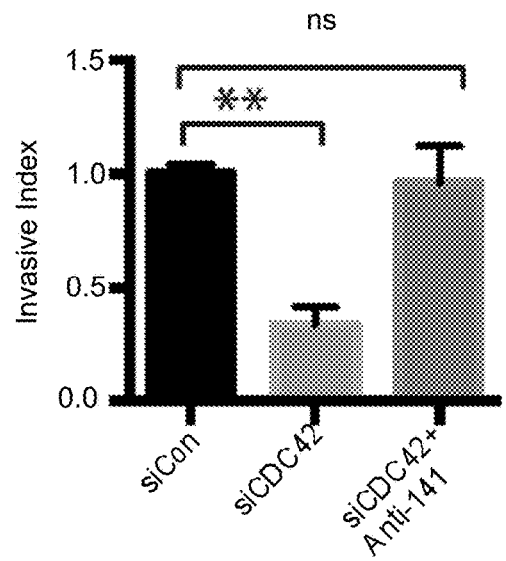

As shown in FIG. 5A, miR-141 over-expression downregulated, to varying degrees, the levels of all 4 proteins. Luciferase reporter assays also indicated that miR-141 inhibited the luciferase activities of the constructs containing the 3'-UTR of RAC1, CDC42, CDC42EP3 or ARPC5 (FIG. 5B). To validate that these molecules represent the functional mediators of the inhibitory effects of miR-141, 'rescue' invasion experiments were performed, in which RAC1 and CDC42 coding constructs that lacked the miR-141 binding site(s) at the 3'-UTRs were overexpressed. As shown in FIG. 5C, overexpression of miR-141 inhibited Du145 cell invasion, but the inhibitory effect was overcome by the expression of non-targetable RAC1 or CDC42 cDNA. Furthermore, miR-141 overexpression suppressed the GTPase activities of RAC1 and CDC42 but not RhoA (FIG. 5D) and, interestingly, RhoA was not predicted to be a direct miR-141 target. Finally, it was observed that the antisense oligos of miR-141 (i.e., anti-141), when transfected into prostate cancer cells, promoted invasion (FIG. 5E). Importantly, siRNA-mediated silencing of RAC1 or CDC42 inhibited Prostate cancer cell invasion, which was 'rescued' by co-transfection of anti-141 (FIG. 5F-5G). These results, taken together, suggest that miR-141 regulates prostate cancer cell motility/invasion via suppressing several members of Rho GTPase signaling pathway.

Example 8

EZH2 Represents Another Novel Target of miR-141

Figure 6A:
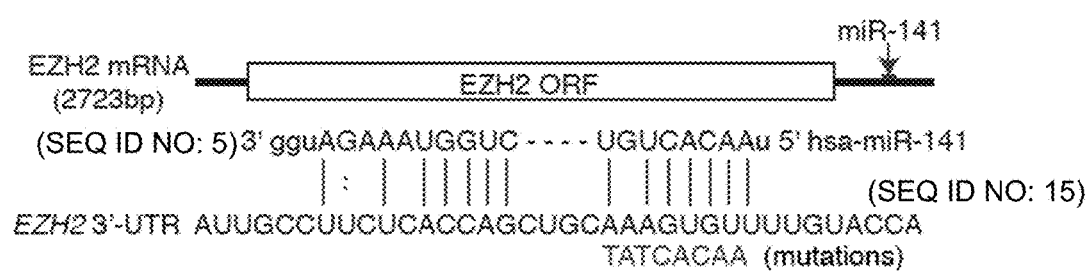
FIGS. 6A-6I show that EZH2 is a direct target of miR-141.
Figure 6B:
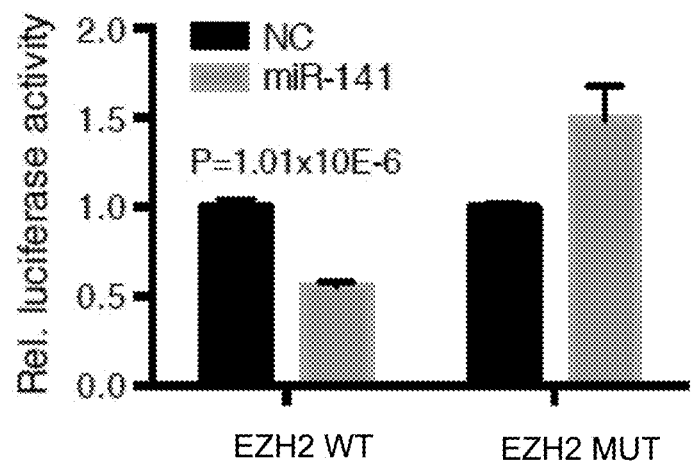
Figure 6C:
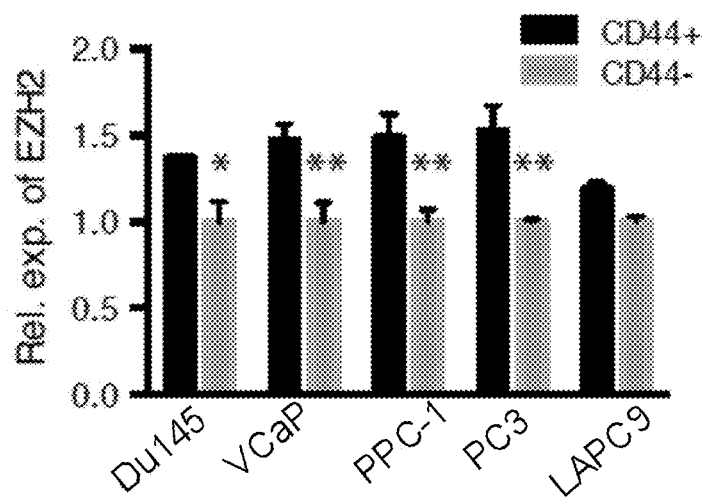
Figure 6D:
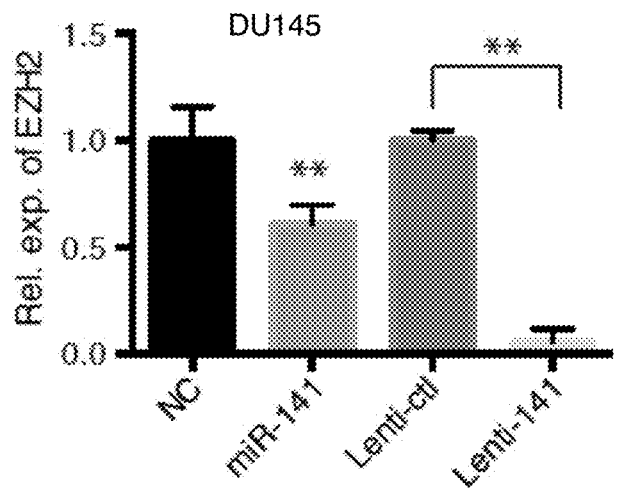
Figure 6E:
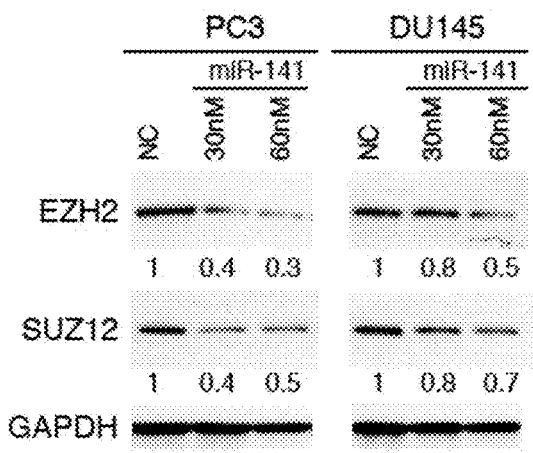
Figure 6F:
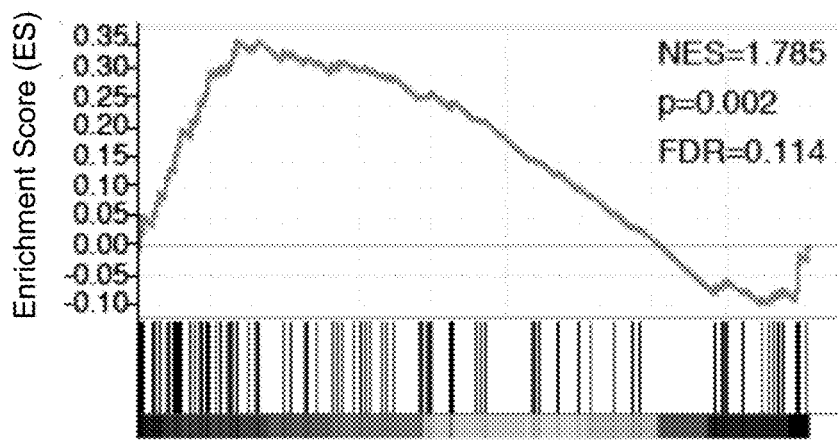
Figure 6G:
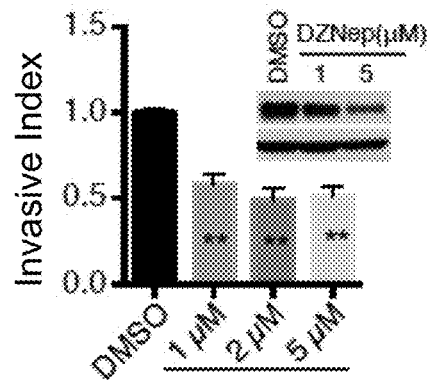
Figure 6H:
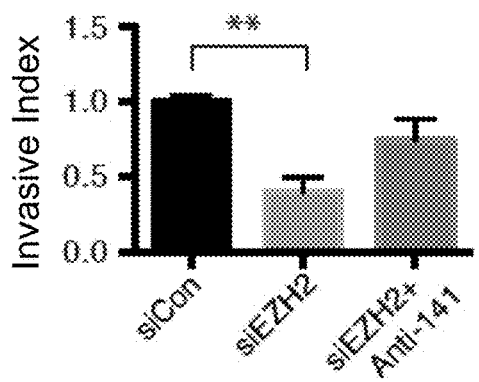
Figure 6I:
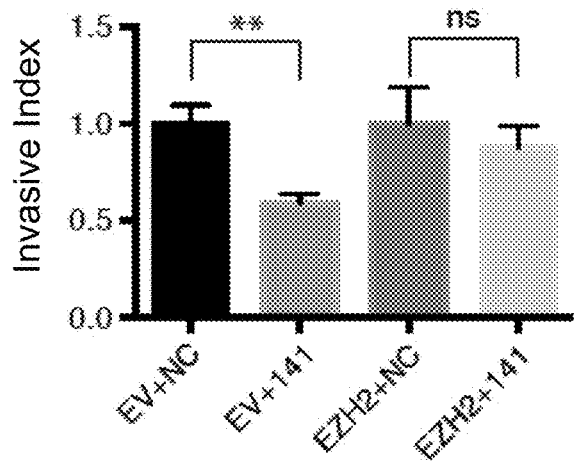

Interestingly, IPA Upstream Regulator analysis implicated EZH2, a histone methyltransferase and a critical component of the PRC2 (Polycomb Repressive Complex 2) that is frequently overexpressed in aggressive forms of prostate and other cancers and is involved in proliferation, cancer sem cell maintenance, invasion and metastasis (43-46), as a miR-141 'upstream regulator' ($P=2.46 \times 10-7$), suggesting that EZH2 might be one of the mediators in miR-141-elicited global gene expression changes. In support, miR-141 induced gene expression profile was associated with "EZH2 Targets DN" in several data sets. Importantly, a putative miR-141 (SEQ ID NO: 1) binding site in the 3'-UTR of EZH2 mRNA (SEQ ID NO: 15) was observed (FIG. 6A). Luciferase reporter assays showed that miR-141 suppressed the luciferase activities of the WT but not mutated EZH2 3'-UTR (FIG. 6B). $CD44^+$ prostate cancer cells generally expressed higher levels of EZH2 mRNA (FIG. 6C) and that miR-141 overexpression significantly reduced both RNA and protein levels of EZH2 in prostate cancer cells (FIGS. 6D-6E). Interestingly, miR-141 expression also reduced the protein levels of SUZ12, another component of the PRC2 complex (FIG. 6E), SUZ12 (repressed) targets were enriched in miR-141 downregulated genes (FIG. 6F), and 1 putative miR-141 binding site at the 3'-UTR of EZH2 was observed. These observations, overall, suggest that EZH2 (and perhaps SUZ12) is a direct target of miR-141. Consistent with this suggestion, DZNep (3-Deazaneplanocin A hydrochloride), a small-molecule EZH2 inhibitor, reduced EZH2 protein and blocked Du145 cell invasion (FIG. 6G). siRNA mediated EZH2 knockdown also inhibited Prostate cancer cell invasion, which was alleviated by anti-141 (FIG. 6H). Finally, miR-141 inhibition of prostate cancer cell invasion could be partially relieved by overexpressing an exogenous EZH2 cDNA that lacked the miR-141 targeting sequence (FIG. 6I). These results, altogether, indicate that EZH2 represents a functionally relevant target of miR-141 in Prostate cancer cells.

Example 9 miR-141 Mimics Inhibits Lung Cancer Cell Proliferation and Invasion

Figure 7A:
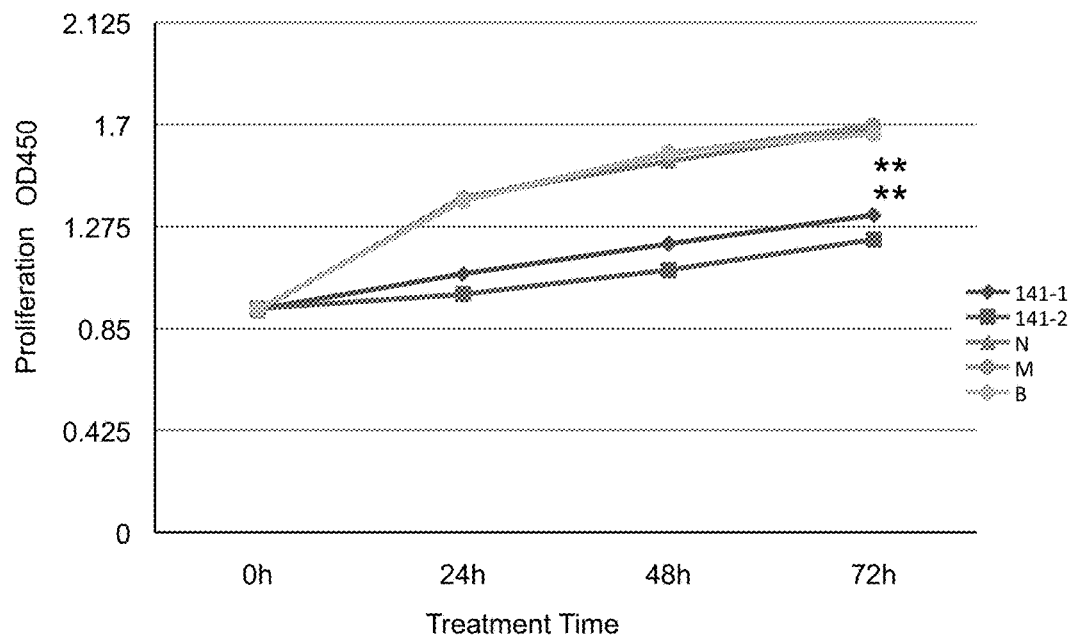
FIGS. 7A-7F shows that miR141 mimics inhibit the invasion/proliferation of lung cancer cells.
Figure 7B:
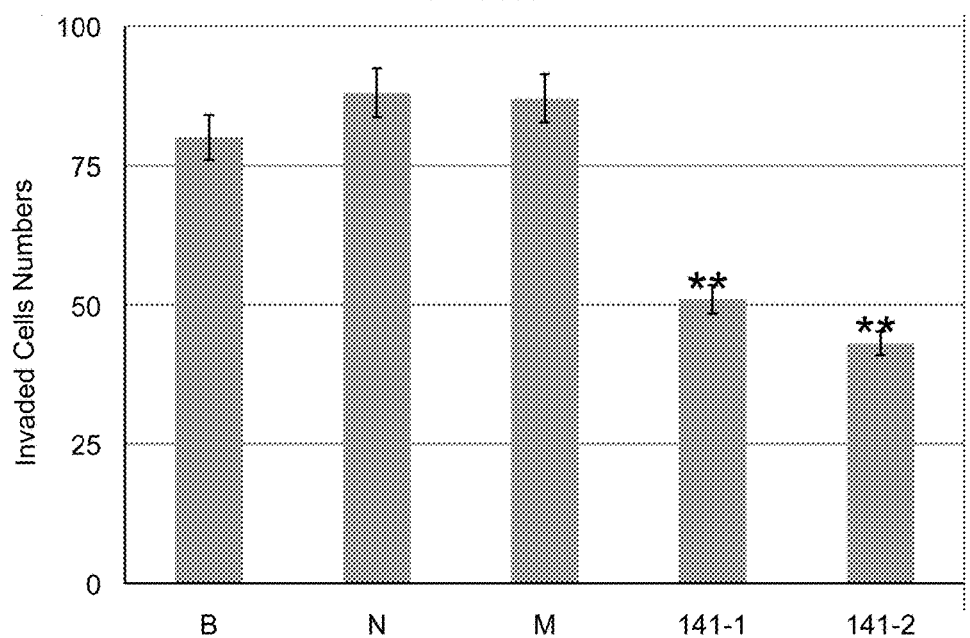
Figure 7C:
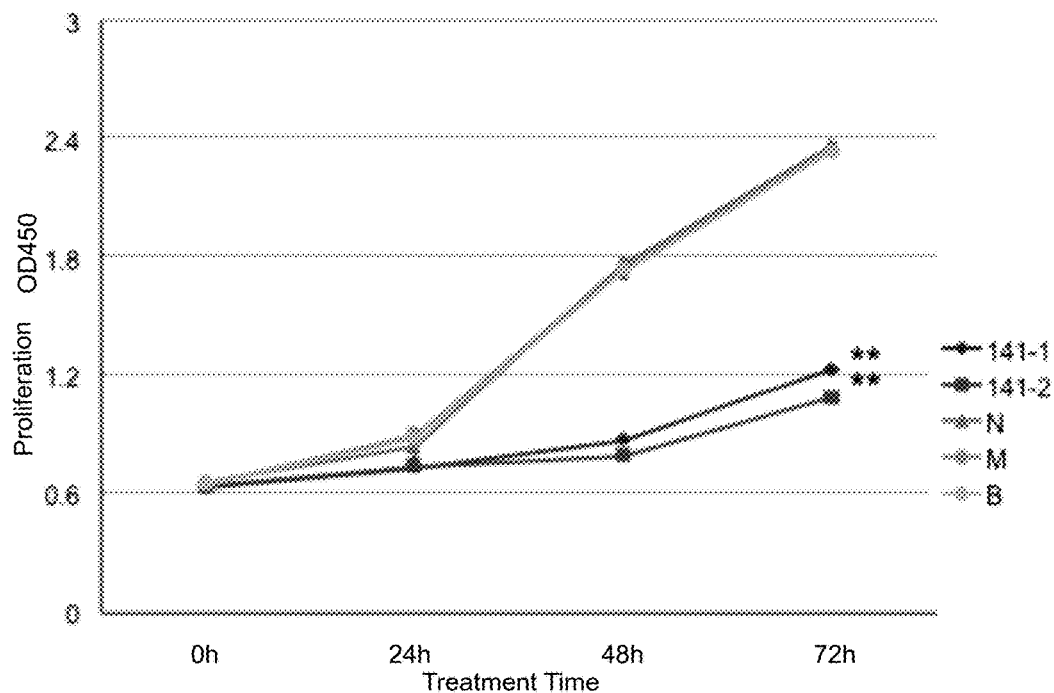
Figure 7D:
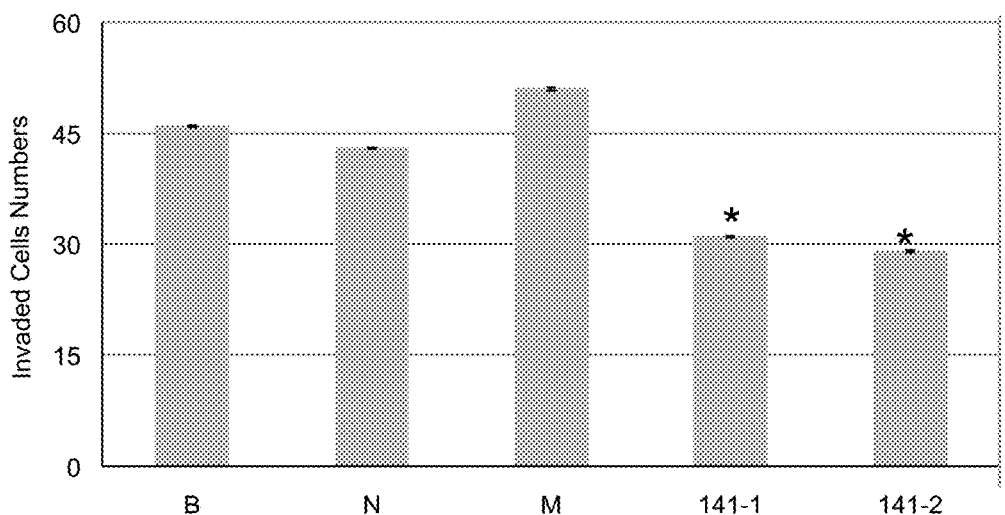
Figure 7E:
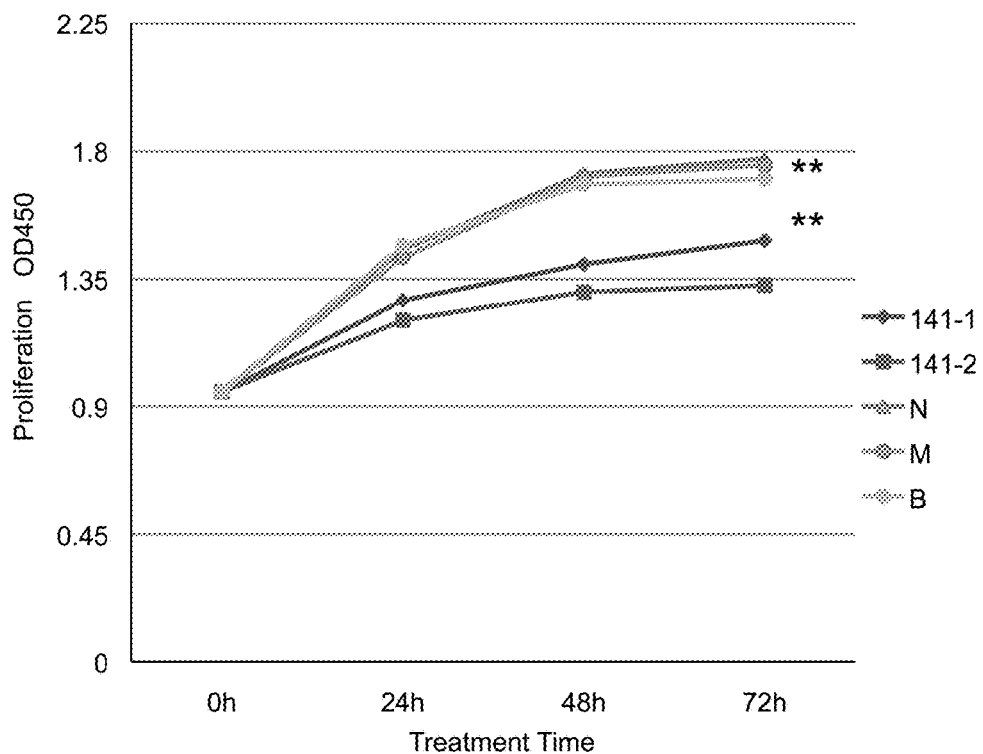
Figure 7F:
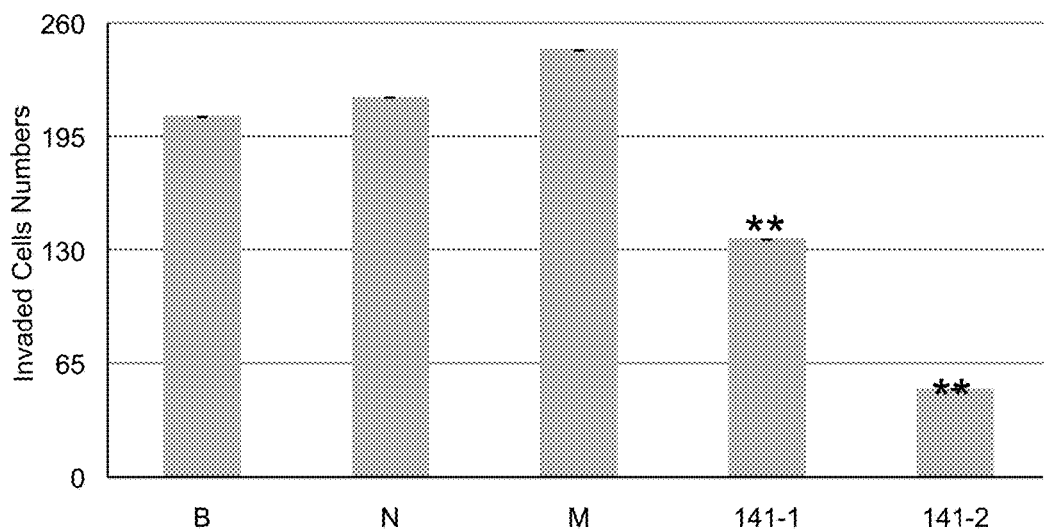

A hallmark of cancer is uncontrolled cell proliferation; cell proliferation assays are commonly used by researchers to study the influence of genes in oncogenesis. A Transwell assay was used to investigate the effect of miR-141 mimics on the proliferation and invasion of the 95D, NCI-H358 lung cancer cells and NCI-H446 non-small lung cancer cells in vitro. Proliferation rate was measured by OD450 value and experiments were repeated twice. Cancer suppression role of miR141-1 and miR141-2 mimics were tested on 95-D lung cancer cells, where miR141-1 and miR141-2 inhibited cancer cell proliferation at 72 hours and invasion as compared to blank control (B), non-sense mimic (N) and medium control (M). miR141-2 inhibited proliferation and invasion of cancer cell more as compared to miR141-1(FIGS. 7A-7B).

miR141 mimics (miR141-1 and miR141-2) were also tested on NCI-H358 lung cancer cells to study their cancer suppression role. Cancer cells proliferation and invasion was significantly inhibited by miR141-1 and miR141-2 mimics as compared to blank control (B), non-sense mimic (N) and medium control (M) (FIGS. 7C-7D).

miR141 mimics (miR141-1 and miR141-2) were also tested on NCI-H446 non-small cells lung cancer cells to study their cancer suppression role. Cancer cells proliferation and invasion was significantly inhibited by miR141-1 and miR141-2 mimics as compared to blank control (B), non-sense mimic (N) and medium control (M). miR141-2 inhibited proliferation and invasion of cancer cell more as compared to miR141-1 (FIGS. 7E-7F).

Example 10 miR-141 Mimics Inhibits Liver Cancer Cell Proliferation and Invasion

Figure 8A:
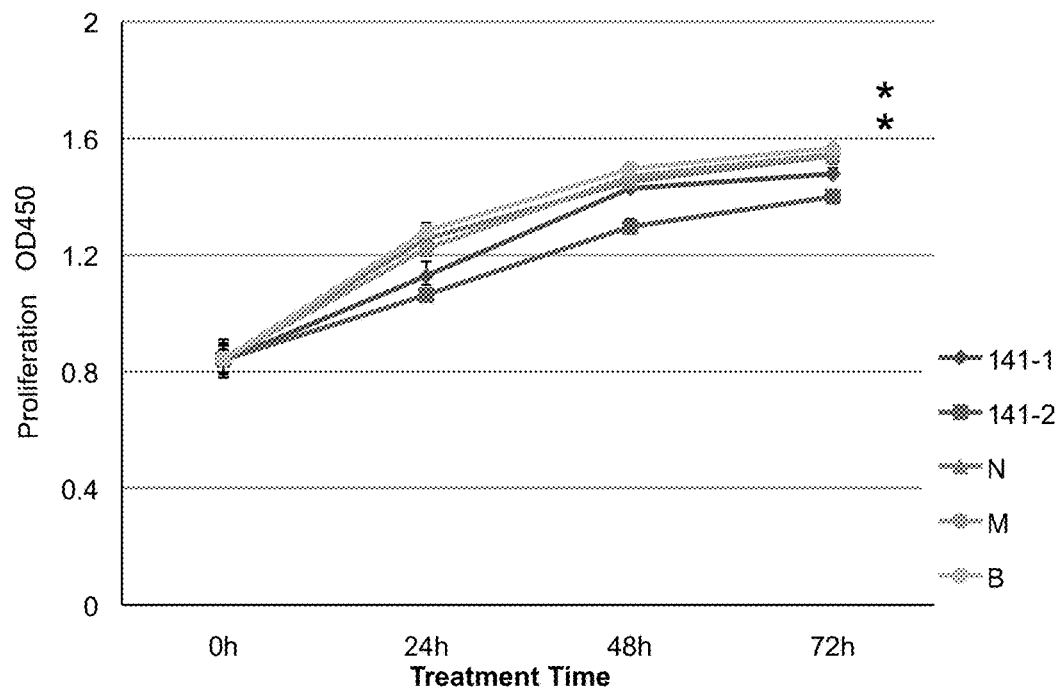
FIGS. 8A-8F show that miR141 mimics inhibit the invasion/proliferation of liver cancer cells.
Figure 8B:
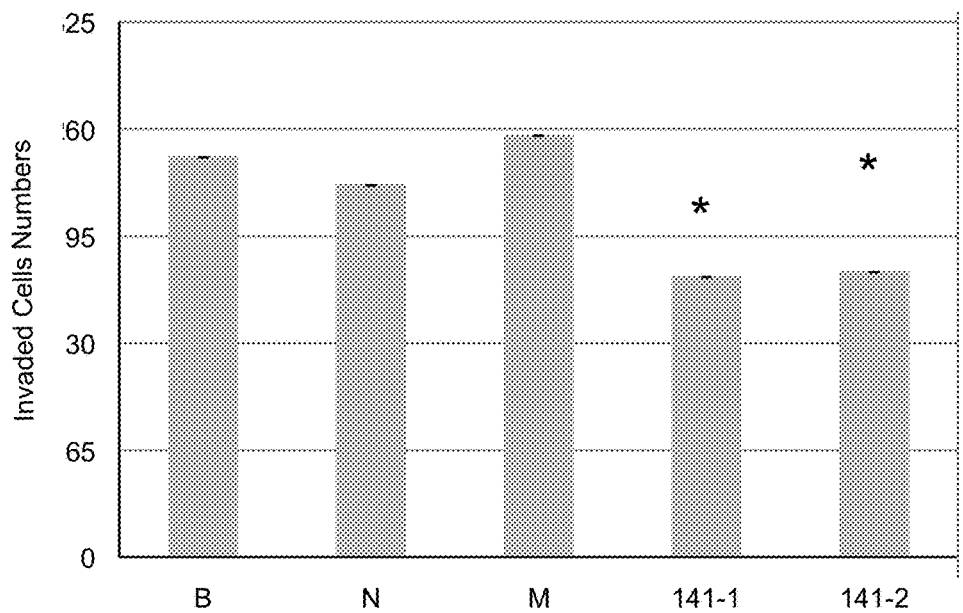
Figure 8C:
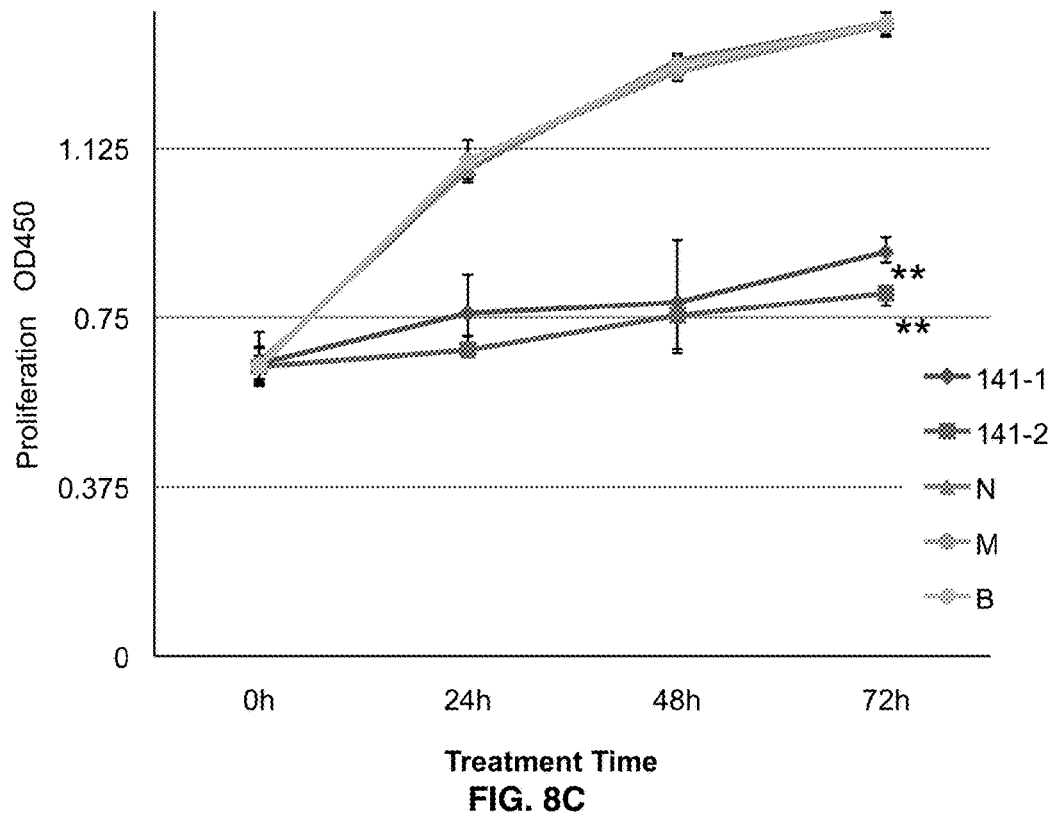
Figure 8D:
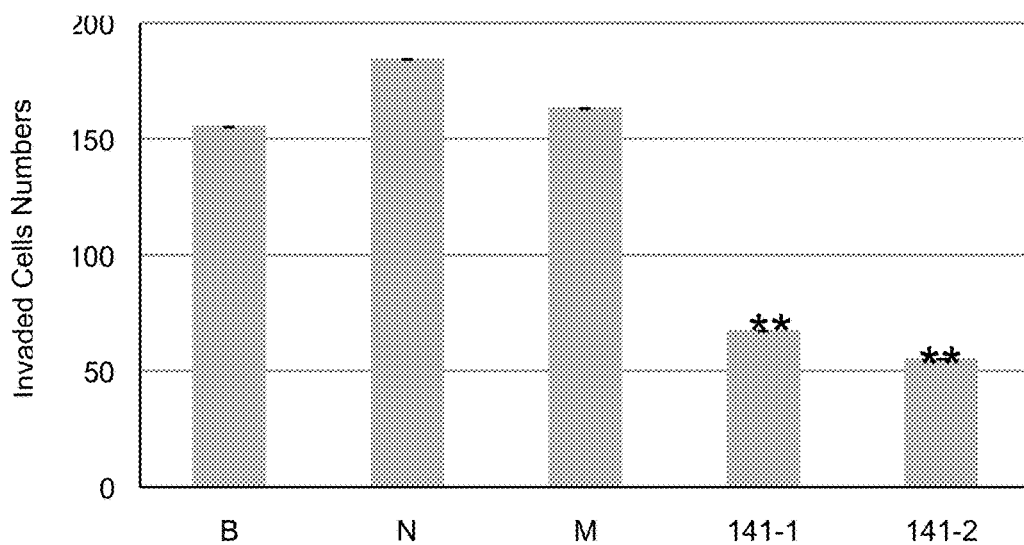
Figure 8E:
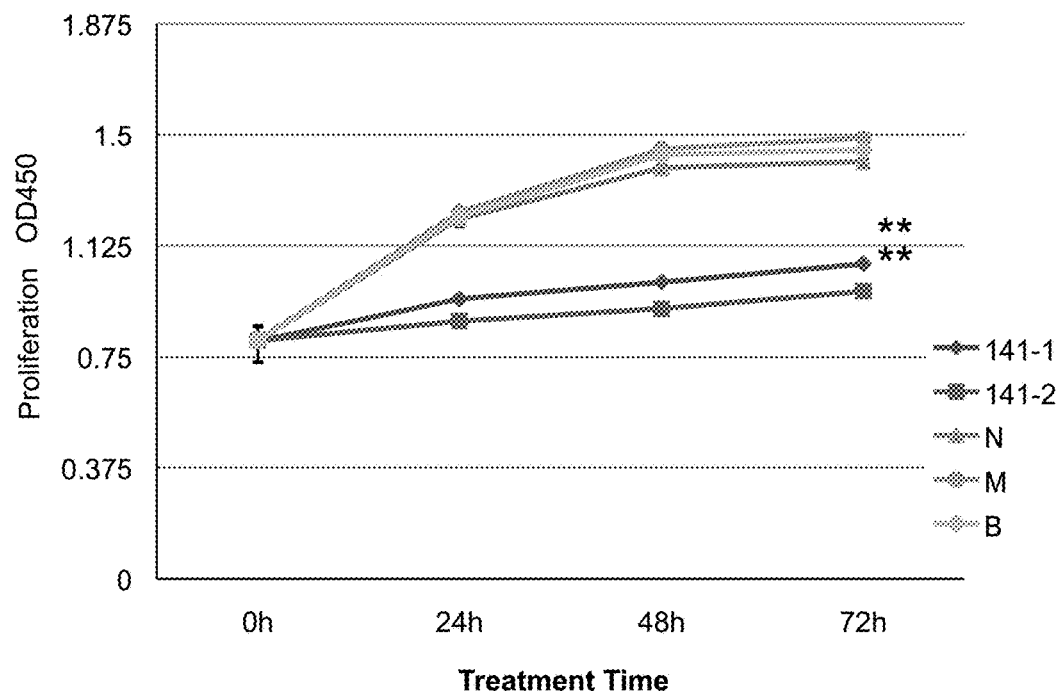
Figure 8F:
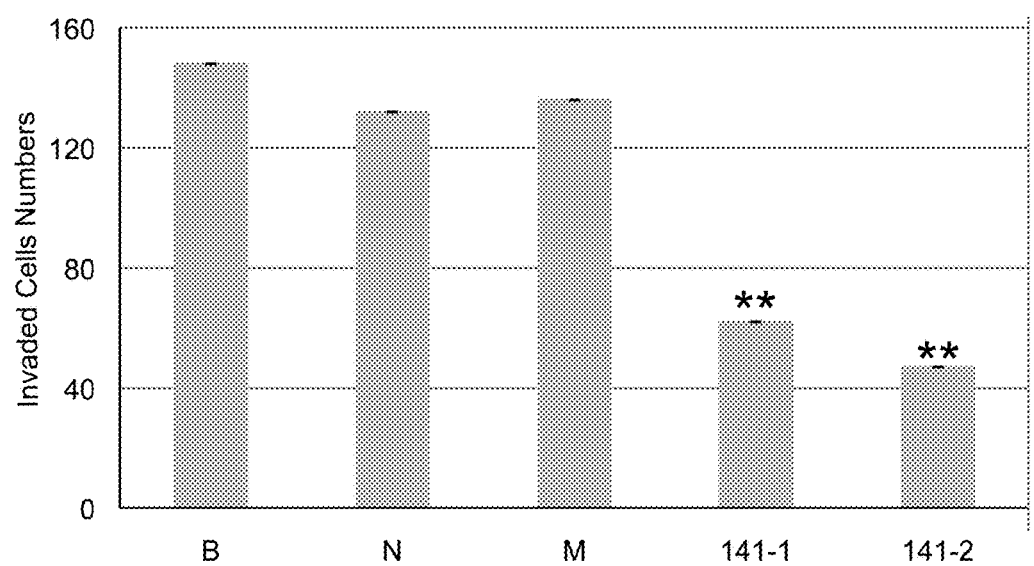

To validate the inhibitory role of miR-141 on proliferation of liver cancer cells, cell proliferation assay was performed Hep3B2.1-7, HepG2 and HL-7702 liver cancer cells. Cell invasion (transwell) assay was performed to further examine if the differential expression of miR-141 was correlated with cell invasion. A Transwell assay was used to investigate the effect of miR-141 mimics on the cell invasion of the Hep3B2.1-7, HepG2 and HL-7702 liver cancer cells in vitro. Proliferation rate was measured by OD450 value and experiments were repeated twice. Cancer suppression role of miR141-1 and miR141-2 mimics were tested on Hep3B2.1-7 liver cancer cells, where miR141-1 and miR141-2 inhibited cancer cell proliferation at 72 hours and cancer cell invasion as compared to blank control (B), non-sense mimic (N) and medium control (M) (FIGS. 8A-8B).

miR141 mimics (miR141-1 and miR141-2) were also tested on HepG2 liver cancer cells to study their cancer suppression role. Cancer cells proliferation and cancer cell invasion was significantly inhibited by miR141-1 and miR141-2 mimics as compared to blank control (B), non-sense mimic (N) and medium control (M) (FIGS. 8C-8D).

miR141 mimics (miR141-1 and miR141-2) were also tested on HL-7702 liver cancer cells to study their cancer suppression role. Cancer cells proliferation and cancer cell invasion was significantly inhibited by miR141-1 and miR141-2 mimics as compared to blank control (B), non-sense mimic (N) and medium control (M). miR141-2 inhibited proliferation and invasion of cancer cell more as compared to miR141-1 (FIGS. 8E-8F).

The following references are cited herein:
1. Kreso et al. Cell Stem Cell 14, 275-291 (2014).
2. Medema, J. P. Nat Cell Biol 15, 338-344 (2013).
3. Tang, D. G. Cell Res 22, 457-472 (2012).
4. Liu et al. Cancer Res 71, 5950-5954 (2011).
5. Adams et al. Curr Biol 24, R762-776 (2014).
6. Feng, X. Y., & Gao, W. Q. Oncogene 33, 135-147 (2014).
7. Pencheva, N. & Tavazoie, S. F. Nat Cell Biol 15, 546-554 (2013).
8. Burk et al. EMBO Report 9, 582-589 (2008).
9. Gregory et al. Nat Cell Biol 10, 593-601 (2008).
10. Park et al. Genes & Dev 22, 894-907 (2008).
11. Korpal et al. Nat Med 17, 1101-1108 (2011).
12. Bracken et al. EMBO J 33, 2040-2056 (2014).
13. Liu et al. Nat Med 17, 211-215 (2011).
14. Liu et al. Cancer Res 72, 3393-3404 (2012).
15. Ma et al. Nature 449, 682-688 (2007).
16. Yun et al. EMBO J 30, 4500-4514 (2011).
17. Liu et al. PLoS Genet. 8, e1002751 (2012).
18. Patrawala et al. Cancer Res 65, 6207-6219 (2005).
19. Collins et al. Cancer Res 65, 10946-10951 (2005).
20. Patrawala et al. Oncogene 25, 1696-1708 (2006).
21. Patrawala et al. D. G. Cancer Res 67, 6796-6805 (2007).
22. Rajasekhar et al. Nat Commun 2, 162 (2011).
23. Qin et al. Cell Stem Cell 10, 556-569 (2012).
24. Domingo-Domenech et al. Cancer Cell 22, 373-388 (2012).
25. Liu et al. Oncotaget 6, 23959-23986 (2015).
26. Rybak et al. Oncotarget 6, 1900-1919 (2015).
27. Kalluri, R. & Weinberg, R. A. J Clin Invest 119, 1420-1428 (2009).
28. Thiery, J. P. & Sleeman, J. P. Nat Rev Mol Cell Biol 7, 131-142 (2006).
29. Iorio et al. Cancer Res 67, 8699-8707 (2007).
30. Mitchell et al. Proc Natl Acad Sci USA 105, 10513-10518 (2008).
31. Cheng et al. PLoS one 6, e17745 (2011).
32. Madhavan et al. Clin Cancer Res 18, 5972-5982 (2012).
33. Li et al. Cancer Res 68, 1820-1825 (2008).
34. Yu et al. Science 339, 580-584 (2013).
35. Lovisa et al. Nat Med. 21, 998-1009 (2015).
36. Jolly et al. Oncotarget 6, 25161-25174 (2015).
37. Liu et al. Stem Cell Reports 2, 78-91 (2013).
38. Zhang et al. Sci. signaling 7, ra91 (2014).
39. Zhang et al. Nat Commun Under revision.
40. Sanz-Moreno et al. Curr Opin Cell Biol 22, 690-696 (2010).
41. Friedl, P. & Alexander, S. Cell 147, 992-1009 (2011).
42. Rottner et al. Curr Opin Cell Biol 23, 569-578 (2011).
43. Varambally et al. Nature 419, 624-629 (2002).
44. Bracken et al. EMBO J 22, 5323-5335 (2003).
45. Kleer et al. Proc. Natl. Acad. Sci. USA 100, 11606-11611 (2003).
46. Cao et al. Oncogene 27, 7274-7284 (2008).
47. Saini et al. Cancer Res. 72, 3618-3630 (2012).
48. Liu et al. Cancer Res. In revision.
49. Cao et al. Cancer Cell 20, 187-199 (2011).
50. Ozen et al. Oncogene 27, 1788-1793 (2008).
51. Ambs et al. Cancer Res 68, 6162-6170 (2008).
52. Szczyrba et al. Mol. Cancer Res. 8, 529-538 (2010).
53. Porkka et al. Cancer Res. 67, 6130-6135 (2007).
54. Hao et al. Cancer Invest 29, 318-324 (2011).
55. Vallejo et al. EMBO J 30, 756-769 (2011).
56. Tong et al. Cancer Gene Ther 16, 206-216 (2009).
57. Waltering et al. Prostate 71, 604-614 (2011).
58. Selth et al. Int J Cancer 131, 652-661 (2012).
59. Xiao et al. Prostate 72, 1514-1522 (2012).
60. Deng, Q. & Tang, D. G. Endocr Relat Cancer 22, T209-220 (2015).
61. Kasinski et al. Oncogene 34, 3547-3555 (2015).
62. Hayes et al. Trends Mol Med 20, 460-469 (2014).
63. Wong et al. Cell Stem Cell 2, 333-44 (2008).
64. Lim et al. Breast Cancer Res 12, R21 (2010).
65. Charafe-Jauffret et al. Oncogene 25, 2273-84 (2006).
66. Onder et al. Cancer Res 68, 3645-54 (2008).
67. Aigner et al. Oncogene 26, 6979-88 (2007).

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method of treating prostate cancer or lung cancer in an individual, comprising:
    administering to the individual a pharmacologically effective amount of a microRNA-141 oligonucleotide or a micro-RNA-141 mimic or a pharmaceutical composition thereof that increases the expression of micro-RNA-141 in a prostate cancer stem cell or a cell associated with the lung cancer.

2. The method of claim 1, wherein the microRNA-141 oligonucleotide has the sequence shown in SEQ ID NO: 1.

3. The method of claim 1, wherein administering the microRNA-141 oligonucleotide or the micro-RNA-141 mimic decreases a mRNA level and a protein level of CD44, EZH2, SUZ12, Rho GTPases or a combination thereof in the prostate cancer stem cell, the cell associated with the lung cancer.

4. The method of claim 1, wherein administering the microRNA-141 oligonucleotide or the micro-RNA-141 mimic upregulates E-Cadherin (CDH1), CLDN7, CLDN3, or cytokeratin genes in the prostate cancer stem cell.

5. The method of claim 1, wherein administering the microRNA-141 oligonucleotide or the micro-RNA-141 mimic downregulates TGFB2, CDK6, SEC23A, ZEB1, MAP2K4, ARPC5, CDC42EP3, CDC42, RAC1, CD44 or VIM genes in the prostate cancer stem cell.

6. The method of claim 1, wherein administering the microRNA-141 oligonucleotide or the micro-RNA-141 mimic inhibits cell proliferation, inhibits invasion, inhibits migration, inhibits tumor growth, inhibits tumor regeneration, or inhibits metastatic potential or a combination thereof in the prostate cancer or the lung cancer.

7. A method of inhibiting proliferation of a lung cancer cell in an individual, comprising:
    administering to the individual a pharmacologically effective amount of a microRNA-141 oligonucleotide or a micro-RNA-141 mimic or a pharmaceutical composition thereof that increases the expression of micro-RNA-141 in the lung cancer cell.

8. The method of claim 7, wherein the microRNA-141 oligonucleotide has the sequence shown in SEQ ID NO: 1.

9. The method of claim 7, wherein administering the microRNA-141 oligonucleotide or the micro-RNA-141 mimic inhibits invasion, migration, tumor growth, tumor regeneration, or metastatic potential of the lung cancer cell.

10. The method of claim 7, wherein administering the microRNA-141 oligonucleotide or the micro-RNA-141 mimic decreases mRNA and protein level of CD44, EZH2, SUZ12, Rho GTPases or a combination thereof in the lung cancer cell.

11. A method of inhibiting metastasis of a prostate cancer in an individual, comprising:
    contacting a prostate cancer stem cell in the individual with a pharmacologically effective amount of a micro-RNA-141 oligonucleotide or a micro-RNA-141 mimic that increases the expression of microRNA-141 in the prostate cancer stem cell.

12. The method of claim 11, wherein the microRNA-141 oligonucleotide has the sequence shown in SEQ ID NO: 1.

13. The method of claim 11, wherein contacting the prostate cancer stem cell with the microRNA-141 oligonucleotide or the micro-RNA-141 mimic decreases the levels of CD44, EZH2, SUZ12, Rho GTPases protein or mRNA or a combination thereof in the cell.

14. The method of claim 11, wherein contacting the prostate cancer stem cell with the microRNA-141 oligonucleotide or the micro-RNA-141 mimic upregulates E-Cadherin (CDH1), CLDN7, CLDN3, or cytokeratin genes therein.

15. The method of claim 11, wherein contacting the prostate cancer stem cell with the microRNA-141 oligonucleotide or the micro-RNA-141 mimic downregulates TGFB2, CDK6, SEC23A, ZEB1, MAP2K4, ARPC5, CDC42EP3, CDC42, RAC1, CD44 or VIM genes therein.

16. The method of claim 11, wherein contacting the prostate cancer stem cell with the microRNA-141 oligonucleotide or the micro-RNA-141 mimic inhibits invasion, inhibits migration, inhibits tumor regeneration, or inhibits metastatic potential or a combination thereof.

* * * * *

SEQUENCE LISTING

```
<160> NUMBER OF SEQ ID NOS: 15

<210> SEQ ID NO 1
<211> LENGTH: 22
<212> TYPE: RNA
<213> ORGANISM: Artificial Sequence
<220> FEATURE:
<223> OTHER INFORMATION: seed sequence of miR-141

<400> SEQUENCE: 1
uaacacuguc ugguaaagau gg                                                22

<210> SEQ ID NO 2
<211> LENGTH: 26
<212> TYPE: DNA
<213> ORGANISM: Artificial Sequence
<220> FEATURE:
<223> OTHER INFORMATION: human CD44 3'-UTR amplified from Du145 genomic
      DNA

<400> SEQUENCE: 2
agagctccac ctacaccatt atcttg                                            26

<210> SEQ ID NO 3
<211> LENGTH: 26
<212> TYPE: DNA
<213> ORGANISM: Artificial Sequence
<220> FEATURE:
<223> OTHER INFORMATION: human CD44 3'-UTR amplified from Du145 genomic
      DNA

<400> SEQUENCE: 3
taagcttgga agtcttcagg agacac                                            26

<210> SEQ ID NO 4
<211> LENGTH: 16
<212> TYPE: RNA
<213> ORGANISM: Artificial Sequence
<220> FEATURE:
<223> OTHER INFORMATION: the region in the CD44 3'-UTR for site-specific
      mutagenesis

<400> SEQUENCE: 4
cuaguguuca agugcc                                                       16

<210> SEQ ID NO 5
<211> LENGTH: 26
<212> TYPE: RNA
<213> ORGANISM: Artificial Sequence
<220> FEATURE:
<223> OTHER INFORMATION: sites in the CD44 3'-UTR targeted by miR-34a

<400> SEQUENCE: 5
uaggccacua uguguuguua cugcca                                            26

<210> SEQ ID NO 6
<211> LENGTH: 25
<212> TYPE: DNA
<213> ORGANISM: Artificial Sequence
<220> FEATURE:
<223> OTHER INFORMATION: human EZH2 3'-UTR amplified from Du145 genomic
      DNA

<400> SEQUENCE: 6
gagctccatc tgctacctcc tcccc                                             25
```

```
<210> SEQ ID NO 7
<211> LENGTH: 29
<212> TYPE: DNA
<213> ORGANISM: Artificial Sequence
<220> FEATURE:
<223> OTHER INFORMATION: human EZH2 3'-UTR amplified from Du145 genomic
      DNA

<400> SEQUENCE: 7
aagcttgaca agttcaagta ttctttatt                                       29

<210> SEQ ID NO 8
<211> LENGTH: 22
<212> TYPE: RNA
<213> ORGANISM: Artificial Sequence
<220> FEATURE:
<223> OTHER INFORMATION: miR-34a Sequence

<400> SEQUENCE: 8
uggcaguguc uuagcugguu gu                                              22

<210> SEQ ID NO 9
<211> LENGTH: 22
<212> TYPE: RNA
<213> ORGANISM: Artificial Sequence
<220> FEATURE:
<223> OTHER INFORMATION: CDK6 Sequence

<400> SEQUENCE: 9
acuguaaaau guauuagugu uu                                              22

<210> SEQ ID NO 10
<211> LENGTH: 22
<212> TYPE: RNA
<213> ORGANISM: Artificial Sequence
<220> FEATURE:
<223> OTHER INFORMATION: ARPC5 sequence

<400> SEQUENCE: 10
agaaaauaaa augucagugu ug                                              22

<210> SEQ ID NO 11
<211> LENGTH: 23
<212> TYPE: RNA
<213> ORGANISM: Artificial Sequence
<220> FEATURE:
<223> OTHER INFORMATION: CDC42EP3 Sequence

<400> SEQUENCE: 11
ccauagcgaa uucuccagug uua                                             23

<210> SEQ ID NO 12
<211> LENGTH: 23
<212> TYPE: RNA
<213> ORGANISM: Artificial Sequence
<220> FEATURE:
<223> OTHER INFORMATION: CDC42 Sequence

<400> SEQUENCE: 12
augcagacuc uucuuaagug uua                                             23

<210> SEQ ID NO 13
<211> LENGTH: 22
<212> TYPE: RNA
<213> ORGANISM: Artificial Sequence
<220> FEATURE:
<223> OTHER INFORMATION: RAC1 Sequence
```

-continued

```
<400> SEQUENCE: 13
guugcagaau uguggagugu uu                                              22

<210> SEQ ID NO 14
<211> LENGTH: 22
<212> TYPE: RNA
<213> ORGANISM: Artificial Sequence
<220> FEATURE:
<223> OTHER INFORMATION: PDHA1 Sequence

<400> SEQUENCE: 14 aggggcuac cagacagugu uc                                               22

<210> SEQ ID NO 15
<211> LENGTH: 36
<212> TYPE: RNA
<213> ORGANISM: Artificial Sequence
<220> FEATURE:
<223> OTHER INFORMATION: putative miR-141 binding site in the 3'-UTR
      of EZH2 mRNA

<400> SEQUENCE: 15
accauguuuu gugaaacguc gaccacucuu ccguua                               36
```